United States Patent [19]

Spry

[11] 4,012,380

[45] Mar. 15, 1977

[54] 7-ACYLAMINO-3-ACYL-2(OR 3)CEPHEMS
[75] Inventor: Douglas O. Spry, Indianapolis, Ind.
[73] Assignee: Eli Lilly and Company, Indianapolis, Ind.
[22] Filed: Dec. 10, 1974
[21] Appl. No.: 531,264
[52] U.S. Cl. ............................. 260/243 C; 424/246
[51] Int. Cl.² ............. C07D 501/24; C07D 501/60
[58] Field of Search ............................... 260/243 C
[56] References Cited

UNITED STATES PATENTS

| 3,488,729 | 1/1970 | Chauvette | 260/243 C |
| 3,647,786 | 3/1972 | Cooper | 260/243 C |
| 3,707,540 | 12/1972 | Amiard et al. | 260/243 C |
| 3,714,154 | 1/1973 | Pfeiffer et al. | 260/243 C |
| 3,897,424 | 7/1975 | Koppel et al. | 260/243 C |
| 3,905,967 | 9/1975 | Berges | 260/243 C |
| 3,947,413 | 3/1976 | Christensen et al. | 260/243 C |

FOREIGN PATENTS OR APPLICATIONS 8,229  5/1971  South Africa ................ 260/243 C Primary Examiner—R. J. Gallagher
Assistant Examiner—Mary C. Vaughn
Attorney, Agent, or Firm—Steven R. Lammert; Everet F. Smith

[57] ABSTRACT

Intermediate C-3 1-hydroxyalkyl or 1-hydroxyarylalkyl cephems, prepared by reacting Grignard reagents at low temperature with 3-formyl-2-cephem compounds, are oxidized to the corresponding 7-acylamino-3-acyl-2(or 3)cephem-4-carboxylic acids and esters thereof, which are useful as antibiotics or as intermediates in preparing antibiotic substances.

15 Claims, No Drawings

7-ACYLAMINO-3-ACYL-2(OR 3)CEPHEMS

BACKGROUND OF THE INVENTION

This invention relates to the cephalosporin class of antibiotics. In particular, this invention relates to cephem compounds having in the 3-position either a 1-hydroxyalkyl (or 1-hydroxyarylalkyl) group, an ester derivative thereof, or a 3-acyl group derived therefrom. The compounds of this invention are therapeutically useful antibiotic compounds or intermediates useful in the preparation of such antibiotics.

Numerous antibiotics of the cephalosporin class have been described, all possessing the same basic ring structure comprising the 4-membered β-lactam ring fused to a 6-membered dihydrothiazine ring, but differing from one another structurally and biologically in many respects. Structurally, the known cephalosporin antibiotics differ in the nature of the 7-acylamino substituent and also in the nature of the substituent in the 3-position on the dihydrothiazine ring. The desacetoxycephalosporanic acids, for example, cephalexin, have a 3-methyl substituent. Numerous cephalosporins having a substituted methyl group in the 3-position have also been described. The desacetylcephalosporins have a 3-hydroxymethyl substituent. The 3-alkylthiomethyl and 3-heteroarylthiomethyl cephems have also been described. More recently, certain 3-methoxymethyl cephems were disclosed in U.S. Pat. No. 3,665,003 and 3-bromomethyl cephems were disclosed in U.S. Pat. Nos. 3,647,788, 3,668,203 and 3,637,678.

In addition to the 3-methyl or 3-substituted methyl cephalosporins, 3-formyl cephalosporins, have been prepared by chromic acid oxidation of the corresponding 3-hydroxymethyl compounds.

Another class of cephalosporins differing in the nature of the substituent at the 3-position was described in Netherlands Pat. No. 7,206,931, wherein certain 3-unsubstituted cephalosporins as well as a method for their preparation by decarbonylation of the corresponding 3-formyl compounds were disclosed.

It is an object of this invention to provide new compounds of the cephalosporin class which are useful as antibiotics or as intermediates in processes for preparing antibiotics.

It is another but more specific object of this invention to provide new structurally unique compounds of the cephalosporin class, wherein a secondary carbinol group (1-hydroxyalkyl or 1-hydroxyarylalkyl), an ester derivative thereof, or an acyl group derived therefrom is attached to the carbon atom in the 3-position of the dihydrothiazine ring.

SUMMARY OF THE INVENTION

This invention is directed to cephem 1-a secondary carbinol group, an ester derivative thereof, or an acyl group derived therefrom, at the C-3 position on the dihydrothiazine ring of the cephem ring system. The novel secondary carbinols, 3-(1-hydroxyalkyl) or 3-(1-hydroxyarylalkyl) cephems, provided by this invention are preferably prepared by reacting a 7-acylamino-3-formyl-2-cephem-4-carboxylic acid ester at low temperature with a Grignard reagent. The product cephem C-3 secondary carbinols can be acylated with, for example, ketene or acetic anhydride, or they can be cyclized via an intramolecular reaction with the C-4 carboxylate group to form the corresponding tricyclic cephalosporin δ-lactones, also active antibiotic compounds. The secondary carbinols can be oxidized with, for example, Jones reagent to the preferred 7-acylamino-3-acyl-2(or 3)-cephem-4-carboxylic acid esters of the present invention. Cleavage of the 7-acylamino moiety provides the corresponding 7-amino-3-acyl cephems which are useful intermediates to preferred antibiotic compounds of the present invention. Removal of the C-4 carboxylic acid ester protecting group provides novel active antibiotic substances, which substances can be employed to combat infections caused by gram-positive and gram negative microorganisms.

DETAILED DESCRIPTION OF THE INVENTION

This invention is directed toward compounds of the formula

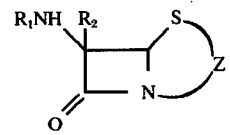

wherein Z is a group of the formula

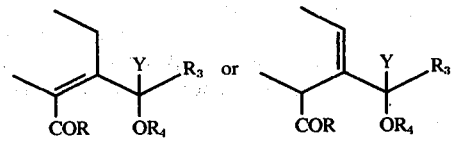

wherein R is a group of the formula —$OR_5$ wherein $R_5$ is hydrogen or a carboxylic acid protecting ester forming group or R taken together with $R_4$ forms a carbon-oxygen single bond;

$R_4$ is hydrogen or acetyl, or $R_4$ taken together with Y forms a carbon-oxygen double bond, or $R_4$ taken together with R forms a carbon-oxygen single bond; and Y is a hydrogen, $C_1$–$C_6$ alkyl, benzyl, or phenyl, or Y taken together with $R_4$ forms a carbon-oxygen double bond; and $R_3$ is hydrogen, $C_1$–$C_6$ alkyl, vinyl, allyl, ethynyl, benzyl or phenyl; with the limitation that when $R_3$ is hydrogen, $R_2$ is methoxy and $R_4$ is only taken together with Y to form a carbon-oxygen double bond; and $R_1$ is hydrogen or an acyl group of the formula

wherein R' is
 (a) $C_1$–$C_6$ alkyl, $C_3$–$C_7$ alkenyl, cyanomethyl, halomethyl, 4-amino-4-carboxybutyl, 4-protected amino-4-protected carboxybutyl; or
 (b) benzyloxy, 4-nitrobenzyloxy or 4-methoxybenzyloxy; or
 (c) the group -R" wherein R" is 1,4-cyclohexadienyl, phenyl or substituted phenyl wherein the substituents are 1–3 halogens, hydroxy, nitro, cyano, trifluoromethyl, $C_1$–$C_4$ alkyl, $C_1$–$C_4$ alkoxy, carboxy, carboxymethyl, hydroxymethyl, aminomethyl or protected aminomethyl; or
 (d) an arylalkyl group of the formula R''—(Y)$_m$—CH$_2$— wherein R'' is as defined above,

Y is O or S, and m is O or 1; or (e) a substituted arylalkyl group of the formula

wherein R''' is R'' as defined above, 2-thienyl or 3-thienyl, W is hydroxy or protected hydroxy, carboxy or protected carboxy, amino or protected amino; or (f) a heteroarylmethyl group of the formula

R''''—CH$_2$— wherein R'''' is 2-thienyl, 3-thienyl, 2-furyl, 3-furyl, 2-thiazolyl, 5-tetrazolyl or 1-tetrazolyl; and R$_2$ is hydrogen or methoxy; and when R$_5$ is hydrogen, the pharmaceutically acceptable non-toxic salts of the acids represented thereby;

with the limitations that when Y and R$_3$ are both other than hydrogen, R$_4$ can only be taken together with R to form a carbon-oxygen single bond; when Z is a group of the formula

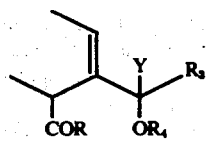

R$_4$ cannot be taken together with R to form a carbon-oxygen single bond; and when R$_4$ is hydrogen, Z is

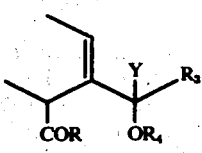

In the foregoing definition of the compounds of the present invention the term "C$_1$-C$_6$ alkyl" refers to methyl, ethyl, n-propyl, n-butyl, isobutyl, pentyl, or n-hexyl, cyclohexyl, and like aliphatic carbon chains. The term "C$_3$-C$_7$ alkenyl" has reference to the unsaturated hydrocarbon chains such as propenyl (allyl), butenyl, pentenyl, hexenyl, cyclohexenyl, heptenyl and the like. "Halomethyl" refers to chloromethyl, bromomethyl, or iodomethyl. Groups defined by the term "C$_1$-C$_6$ alkoxy" are methoxy, ethoxy, isopropoxy, tert-butoxy, neopentoxy, cyclohexyloxy and like groups.

When in the above definition R'' represents a substituted phenyl group, R'' can be a mono or disubstituted halophenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono or dihydroxyphenyl group such as 4-hydroxyphenyl, 3-hydroxyphenyl, 2,4-dihydroxyphenyl and the like; a mononitrophenyl group such as 3- or 4-nitrophenyl; a cyanophenyl group, for example, 4-cyanophenyl; a mono or disubstituted lower alkylphenyl group such as 4-methylphenyl, 2,4-dimethylphenyl, 2-methylphenyl, 4-isopropylphenyl, 4-ethylphenyl, 3-n-propylphenyl and the like; a mono or disubstituted lower alkylphenyl ether for example, 2,6-dimethoxyphenyl, 4-methoxyphenyl, 3-ethoxyphenyl, 4-isopropoxyphenyl, 4-tert-butoxyphenyl, 3-ethoxy-4-methoxyphenyl and the like. Also, R'' represents disubstituted phenyl groups wherein the substitutents can be different for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and like disubstituted phenyl groups bearing different substituents.

The term, "protected amino" as employed in the above definition has reference to an amino group substituted with one of the commonly employed amino blocking groups such as the tert-butoxycarbonyl group (t-BOC); the benzyloxycarbonyl group, the 4-methoxybenzyloxycarbonyl group, the 4-nitrobenzyloxycarbonyl group, the 2,2,2-trichloroethoxycarbonyl group, the 1-carbomethoxy-2-propenyl group formed with methyl acetoacetate, and the trimethylsilyl group. Like amino protecting groups such as those described by J. W. Barton in "Protective Groups in Organic Chemistry," J. F. W. McOmie, Ed., Plenum Press, New York, N.Y., 1973, Chapter 2 shall be recognized as suitable.

The term "protected hydroxy" has reference to the readily cleavable groups formed with an hydroxyl group such as the formyloxy group, the chloroacetoxy group, the benzyloxy group, the benzhydryloxy group, the trityloxy group, the 4-nitrobenzyloxy group, the trimethylsilyloxy group, and the like. Other hydroxy protecting groups, including those described by C. B. Reese in "Protective Groups in Organic Chemistry", supra, Chapter 3 shall be considered as within the term "protected hydroxy" as used herein.

The term "protected carboxy" has reference to a carboxy group which has been protected by one of the commonly used carboxylic acid protecting ester groups employed to block or protect the carboxylic acid functionality while reactions involving other functional sites of the compound are carried out. Such protected carboxy groups are noted for their ease of cleavage by hydrolytic or by hydrogenolytic methods to the corresponding carboxylic acid. Examples of carboxylic acid protecting groups include tert-butyl, benzyl, 4-methoxybenzyl, C$_2$-C$_6$ alkanoyloxymethyl, 2-iodoethyl, 4-nitrobenzyl, diphenylmethyl (benzhydryl), phenacyl, p-halophenacyl, dimethylallyl, 2,2,2-trichloroethyl and like ester forming moieties. The nature of such ester forming groups is not critical so long as the ester formed therewith is stable under the reaction conditions described hereinafter. Furthermore, other known carboxy protecting groups such as those described by E. Haslam in "Protective Groups in Organic Chemistry", supra, Chapter 5, shall be recognized as suitable. Preferred carboxylic acid protecting groups are benzhydryl, dimethylallyl, tert-butyl, 4-methoxybenzyl, and 2-iodoethyl; most preferred ae benzhydryl, 4-methoxybenzyl and tert-butyl.

In the foregoing definitions, hydroxy, amino, and carboxy protecting groups are not exhaustively defined. The function of such groups is to protect the reactive functional groups during the preparation of the desired products and then be removed without disrupting the remainder of the molecule. Many such protecting groups are well known in the art and the use of other groups equally applicable to the process and compounds of the present invention shall be recognized as suitable. Thus, there is no novelty or inventiveness asserted with regard to the protecting groups alluded to in this specification.

Illustrative of the acyl groups,

as defined above are acetyl, propionyl, butyryl, hexanoyl, heptanoyl, 2-pentenoyl, acryloyl, 5-aminoadipoyl, chloroacetyl, bromoacetyl and the like.

Representative of the acyl groups

are benzoyl, 2,6-dimethoxybenzoyl, 4-chlorobenzoyl, 4-methylbenzoyl, 3,4-dichlorobenzoyl, 4-cyanobenzoyl, 3-bromobenzoyl, 3-aminobenzoyl, 4-nitrobenzoyl and the like.

Illustrative of the acyl groups

when R' is a group of the formula R''—(Y)$_m$—CH$_2$— and m is 0, are cyclohexa-1,4-diene-1-acetyl, phenylacetyl, 4-chlorophenylacetyl, 3-hydroxyphenylacetyl, 3-cyanophenylacetyl, 4-hydroxy-3-methylphenylacetyl, 4-bromophenylacetyl, 4-ethoxyphenylacetyl, 4-nitrophenylacetyl, 3,4-dimethoxyphenylacetyl and the like; and when m is 1 and Y is O, representative acyl groups are phenoxyacetyl, 3-hydroxyphenoxyacetyl, 4-chlorophenoxyacetyl, 3,4-dichlorophenoxyacetyl, 2-chlorophenoxyacetyl, 4-methoxyphenoxyacetyl, 2-ethoxyphenoxyacetyl, 3,4-dimethylphenoxyacetyl, 4-isopropylphenoxyacetyl, 3-cyanophenoxyacetyl, 3-nitrophenoxyacetyl and like substituted phenoxyacetyl groups; and when m is 1 and Y is S, representative phenylthioacetyl groups are phenylthioacetyl, 2,5-dichlorophenylthioacetyl, 3-chloro-4-fluorophenylthioacetyl, 4-cyanophenylthioacetyl, 3-bromophenylthioacetyl, and like acyl groups.

Illustrative of the acyl groups when R' is a substituted arylalkyl group of the formula

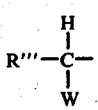

are the hydroxy substituted arylalkyl groups such as the 2-hydroxy-2-phenylacetyl group of the formula

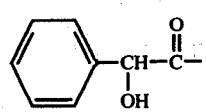

or the 2-formyloxy-2-phenylacetyl group of the formula

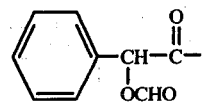

and similar groups wherein the phenyl ring is substituted, for example, 2-hydroxy-2-(4-methoxyphenyl)acetyl, 2-hydroxy-2-(3-chloro-4-hydroxyphenyl)acetyl, 2-formyloxy-2-(4-hydroxyphenyl)acetyl, 2-hydroxy-2-(3-bromophenyl)acetyl, 2-formyloxy-2-(3,5-dichloro-4-hydroxyphenyl)acetyl, 2-formyloxy-2-(3-chloro-4-methoxyphenyl)acetyl, 2-hydroxy-2-(3-chlorophenyl)acetyl and like groups.

Representative of the acyl groups when R' is a carboxy or alkoxycarbonyl substituted arylalkyl group are 2-carboxy-2-phenylacetyl, 2-tert-butoxycarbonyl-2-phenylacetyl, 2-benzyloxycarbonyl-2-(4-chlorophenyl)acetyl, 2-carboxy-2-(4-methoxyphenyl)acetyl, 2-carboxy-2-(3-nitrophenyl)acetyl, and like groups.

When R' is an amino substituted arylalkyl group or a derivative thereof, acyl groups represented thereby include 2-amino-2-phenylacetyl, 2-amino-2-(1,4-cyclohexadien-1-yl)acetyl, 2-tert-butoxycarbonylamino-2-phenylacetyl, 2-amino-2-(4-hydroxyphenyl)acetyl, and like acyl groups.

Representative of the acyl group

when R' is a heteroarylmethyl group of the formula R'''—CH$_2$— are 2-thienylacetyl, 3-thienylacetyl, 2-furylacetyl, a 2-thiazolylacetyl group of the formula

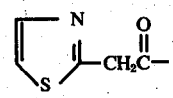

a 1-tetrazolylacetyl group of the formula

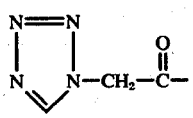

or a 5-tetrazolylacetyl group of the formula

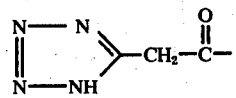

The compounds of the present invention of the formula

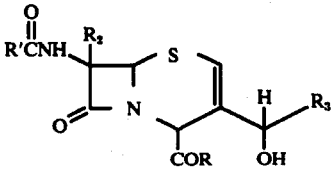

are prepared by a process comprising reacting a compound of the formula

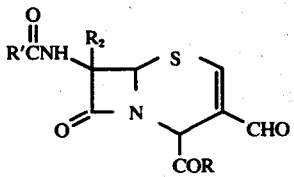

with about 3 equivalents of a Grignard reagent of the formula R₃MgX in an ethereal solvent at a temperature between −78° and −30° wherein in the above formula R, R′, R₂ and R₃ are as defined hereinabove with the limitation that R cannot be 4-nitrobenzyloxy.

Ester derivatives of the aforementioned carbinols are prepared by conventional acylating procedures, such comprising reaction with ketene, or reaction with an acid chloride or mixed anhydride in the presence of a tertiary amine base. The tricyclic cephalosporin δ-lactones provided by this invention, internal esters of the formula

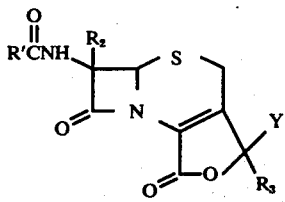

are generally isolated as by-products in the reaction of Grignard reagents with 3-formyl-2-cephem esters. Lactones of the above formula wherein Y and R₃ are other than hydrogen can be prepared by the reaction of suitable Grignard reagents with 3-acyl cephem esters, without regard to whether the cephem double bond is in the 2- or 3- position.

The present invention also provides a process for the preparation of 7-acylamino-3-(1-hydroxyalkyl or 1-hydroxyarylalkyl)cephem-4-carboxylic acid esters (secondary carbinols), compounds which are useful primarily as intermediates to the biologically more active 3-acyl cephems. Generally, the secondary carbinols are prepared by the reaction of Grignard reagents with known 3-formyl cephalosporin derivatives. The reaction of Grignard reagents with aldehydes or ketones to provide secondary or tertiary carbinols respectively is one of many well known synthetically useful reactions of Grignard reagents. The use of such reagents to prepare carbinols has been well documented in the chemical literature. However, the potential utility of such carbanionic reagents has not been realized with β-lactam antibiotics because of the known lability of the β-lactam ring system in the presence of nucleophilic reagents. It has now been found, however, that by lowering the reaction temperature, Grignard reagents can be made to react selectively with a 3-formyl or 3-acyl carbonyl group on a cephem ring system without attacking the susceptible β-lactam entity.

Several methods for the preparation of 3-formyl-2-cephem derivatives, starting materials for the compounds of the present invention, have been disclosed. These compounds were first described by Woodward et al. [*Journal of the American Chemical Society*, 88, 852 (1966)] as intermediates in the total synthesis of Cephalosporin C. In general the 3-formyl cephem compounds are prepared by oxidation of the corresponding 3-hydroxymethyl cephem derivatives with manganese dioxide or chromium trioxide, particularly and preferably chromium trioxide in sulfuric acid/water, commonly referred to as Jones Reagent. A process for the preparation of 7-acylamino-3-formyl-3-cephem-4-carboxylic acid esters has been described by Chamberlin et. al. in the *Journal of Medicinal Chemistry*, 10, 967 (1967) wherein the corresponding 7-acylamino-3-hydroxymethyl-3-cephem-4-carboxylic acids are first esterified by known procedures, and the resulting esters are oxidized to the 3-formyl derivatives with manganese dioxide or Jones Reagent as described hereinabove.

Alternatively, the 7-acylamino-3-hydroxymethyl-2-cephem-4-carboxylic acids can be oxidized directly to their 3-formyl derivatives using 2,3-dichloro-5,6-dicyano-1,4-benzoquinone as described in U.S. Pat. No. 3,682,903 and then esterified.

The 7-acylamino-7-methoxy-3-formyl-2-cephem-4-carboxylic acids and ester derivatives thereof, can be prepared from the corresponding 7-acylamino-7-methoxy-3-acetoxymethyl cephem derivatives, for example 7-methoxy cephalothin, by procedures identical to those described hereinabove for the conversion of non-methoxylated cephalosporins to the respective 3-formyl cephem starting materials.

Illustrative of the 3-formyl-2-cephem derivatives useful as starting materials in preparing the compounds of the present invention are:

benzhydryl 7-(2-thienylacetamido)-3-formyl-2-cephem-4-carboxylate, tert-butyl 7-acetamido-3-formyl-2-cephem-4-carboxylate, 4′-methoxybenzyl 7-phenylacetamido-7-methoxy-3-formyl-2-cephem-4-carboxylate, benzhydryl 7-phenoxyacetamido-3-formyl-2-cephem-4-carboxylate, 2′-iodoethyl 7-(2-furylacetamido)-3-formyl-2-cephem-4-carboxylate, benzhydryl 7-(5-amino-5-tert-butoxycarbonylvaleramido)-3-formyl-2-cephem-4-carboxylate, 4′-methoxybenzyl 7-(2-thienylacetamido)-3-formyl-2-cephem-4-carboxylate, benzhydryl 7-(4-chlorophenoxyacetamido)-7-methoxy-3-formyl-2-cephem-4-carboxylate, 4′-nitrobenzyl 7-phenylacetamido-3-formyl-2-cephem-4-carboxylate, tert-butyl 7-(5-tert-butoxycarbonylamino-5-tert-butoxycarbonylvaleramido)-3-formyl-2-cephem-4-carboxylate, benzhydryl 7-(3-thienylacetamido)-3-formyl-2-cephem-4-carboxylate, 4′-methoxybenzyl 7-benzamido-3-formyl-2-cephem-4-carboxylate, 2′-iodoethyl 7-(2-formyloxy-2-phenylacetamido)-7-methoxy-3-formyl-2-cephem-4-carboxylate, tert-butyl 7-chloroacetamido-3-formyl-2-cephem-4-carboxylate, benzhydryl 7-(4-nitrobenzyloxycarbonylamino)-3-formyl-2-cephem-4-carboxylate, tert-butyl 7-(1-tetrazolylacetamido)-7-methoxy-3-formyl-2-cephem-4-carboxylate, and 4'-methoxybenzyl 7-(2-tert-butoxycarbonyl-2-phenylacetamido)-2-cephem-4-carboxylate.

The process provided by the present invention is a general reaction and may be performed with a wide variety of 3-formyl-2-cephem starting materials. 3-Formyl-2-cephems having a 7-(2-thienylacetamido) side chain are a preferred group of starting materials, but only because of the availability of such compounds from readily available cephalothin. 3-Formyl-2-cephems bearing other 7-acylamino side chains can be prepared and employed as starting materials with equal success.

In general, the process of this invention is carried out by reacting a 3-formyl-2-cephem compound with about 3 equivalents of a Grignard reagent in an anhydrous ethereal solvent at a temperature between −78° and −30° C., and, after the reaction is complete and before the reaction mixture is allowed to warm above the reaction temperature, excess acid is added.

Because of the nature of the Grignard reactant, the process must be carried out under anhydrous conditions. To maintain anhydrous conditions the reaction is usually performed under an inert atmosphere such as argon or nitrogen; however, other conventional less stringent experimental procedures designed to exclude moisture from the reaction mixture can be employed without a substantial detrimental effect on the reaction.

Exemplary of known Grignard reagents suitable for the process of the present invention are $C_1$–$C_6$ alkylmagnesium halides, for example methylmagnesium bromide, ethylmagnesium iodide, isopropylmagnesium chloride, n-butylmagnesium bromide, cyclohexylmagnesium iodide; arylmagnesium halides such as phenylmagnesium bromide or naphthylmagnesium iodide; benzylmagnesium halides including benzylmagnesium chloride, bromide or iodide; allylmagnesium halides; vinylmagnesium halides and ethynylmagnesium halides. Preferred Grignard reagents include $C_1$–$C_3$ alkylmagnesium halides, benzylmagnesium halides, and phenylmagnesium halides.

Suitable ethereal solvents for the process of the present invention are diethyl ether, dipropyl ether, diisopropyl ether, dibutyl ether, butyl ethyl ether, ethylene glycol dimethyl ether, dioxane and tetrahydrofuran. Preferred solvents are 1,4-dioxane diethyl ether and tetrahydrofuran. Tetrahydrofuran is most preferred.

The reaction of Grignard reagents with 7-acylamino-3-formyl-2-cephem-4-carboxylic acids and esters can be effected at temperatures ranging from about −78° to about −30° C., preferably from −78° to about −50° C., and most advantageously from −78° to −60° C.

The reaction is usually complete after about 3 minutes to about 1 hour, depending on the solvent, the particular 3-formyl-2-cephem employed, the Grignard reagent, and the temperature at which the reaction is performed. Generally, at the preferred reaction temperature the carbinol formation is complete within about 5 minutes.

After the reaction is complete, and before the reaction mixture is allowed to warm above the reaction temperature, the mixture is acidified with an excess of an aqueous acid, usually 1 N. hydrochloric acid. This procedure serves not only to destroy any excess Grignard reagent and the intermediate oxymagnesium halide complex, but also to neutralize any anionic sites on the cephem molecule, i.e., at C-4 or at amide NH, believed also to be generated by the Grignard reagent. This procedure eliminates or considerably diminishes the possiblity of unwanted side reactions as the mixture warms to about 0° C., the temperature at which the work-up of the reaction mixture is carried out.

Maximum yields of the secondary carbinol products are achieved by employing about 3 equivalents of Grignard reagent for each equivalent of 3-formyl-2-cephem starting material. The carbinol forming process of this invention can be performed with less than 3 equivalents of Grignard reagent; however, yields of the desired cephem carbinols are substantially lower. Alternatively, a relatively large excess, for example, 5 to 10 equivalents of Grignard reagent for each equivalent of 3-formyl cephem may be employed with but little detrimental effect on the conversion if such excess is destroyed before the reaction mixture is allowed to warm above dry ice-acetone temperature. No by-products resulting from attack on the β-lactam by the Grignard reagent are observed, thus demonstrating the stability of that ring system under the conditions described herein.

Biologically active highly crystalline cephem γ-lactones of the formula

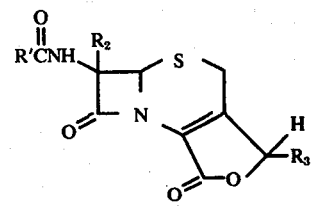

are also isolated as products from the above described process. Generally, the yield of the lactone is substantially lower that that of the product carbinol. However, when 4'-nitrobenzyl 7-(2-thienylacetamido)-3-formyl-2-cephem-4-carboxylate is reacted with methylmagnesium bromide under the conditions set forth hereinabove, only the tricyclic 7-(2-thienylacetamido)-3-(1-hydroxyethyl)-3-cephem-4-carboxylic acid lactone is isolated.

The cephem lactone and secondary carbinols are isolated as mixtures of diastereoisomers. These mixtures can be resolved either by fractional recrystallization of the mixture or by careful fractionation of a column chromatographic separation. Hereinafter, when reference is made to a cephem secondary carbinol or lactone or acetate derivative thereof, such reference is to a diastereoisomeric mixture, unless specified otherwise.

The preferred conditions and procedures employed in the preparation of the secondary carbinols of this invention are summarized in the following description of the preparation of benzhydryl 7-acetamido-3-(1-hydroxypropyl)-2-cephem-4-carboxylate: To a cold (−73° C.) solution of 10 mmoles of benzhydryl 7-acetamido-3-formyl-2-cephem-4-carboxylate in 60 ml. of tetrahydrofuran is added 30 mmoles of ethylmagnesium bromide in tetrahydrofuran. After 4 minutes, 10 ml. of 1N.HCl is added, and the reaction mixture is allowed to warm to ca. 0°. The product obtained after washing the reaction mixture with dilute acid is chromatographed on silica gel to provide benzhydryl 7-acetamido-3-(1-hydroxypropyl)-2-cephem-4-carboxylate as a mixture of diastereomers. The isomers can be separated by careful fractionation. Prolonged elution of the chromatographic column provides a quantity (approximately 5 percent yield when starting material is a benzhydryl ester) of 7-acetamido-3-(1-hydroxypropyl)-3-cephem-4-carboxylic acid lactone, a by-product of the Grignard reaction.

Exemplary of the cephem secondary carbinols of th present invention are:

dimethylallyl 7-acetamido-7-methoxy-3-(α-hydroxybenzyl)-2-cephem-4-carboxylate, benzhydryl 7-phenoxyacetamido-3-(1-hydroxypropyl)-2-cephem-4-carboxylate, tert-butyl 7-(2-tert-butoxycarbonyl-2-phenylacetamido)-3-(1-hydroxy-2-phenylethyl)-2-cephem-4-carboxylate, 7-phenylacetamido-3-(1-hydroxyethyl)-2-cephem-4-carboxylic acid, 4'-methoxybenzyl 7-(5-tetrazolylacetamido)-7-methoxy-3-(1-hydroxyallyl)-2-cephem-4-carboxylate, benzhydryl 7-(2,5-dichlorophenylthioacetamido)-3-(1-hydroxy-2-methylpropyl)-2-cephem-4-carboxylate, 2'-iodoethyl 7-[4-(4-nitrobenzyloxycarbonylamino)-4-(4-nitrobenzyloxycarbonyl)valeramido]-7-methoxy-3-(α-hydroxybenzyl)-2-cephem-4-carboxylate, benzyl 7-(2-iodoacetamido)-3-(1-hydroxybutyl)-2-cephem-4-carboxylate, benzhydryl 7-[2-(1,4-cyclohexadienyl)-2-aminoacetamido]-7-methoxy-3-(1-hydroxy-2-phenylethyl)-2-cephem-4-carboxylate, 4'-methoxybenzyl 7-phenylthioacetamido-3-cyclohexylhydroxymethyl-2-cephem-4-carboxylate, tert-butyl 7-(2-benzyloxy-2-phenylacetamido)-3-(1-hydroxy-2-methylpropyl)-2-cephem-4-carboxylate, dimethylallyl 7-(4-trifluoromethylphenylacetamido)-3-(1-hydroxyethyl)-2-cephem-4-carboxylate, dimethylallyl 7-(2-thienylacetamido)-7-methoxy-3-cyclohexylhydroxymethyl-2-cephem-4-carboxylate, benzhydryl 7-(2-furylacetamido)-3-(α-hydroxybenzyl)-2-cephem-4-carboxylate, benzhydryl 7-(4-nitrobenzyloxycarbonylamino)-3-(1-hydroxyethyl)-2-cephem-4-carboxylate, 7-chloroacetamido-3-(1-hydroxypropyl)-2-cephem-4-carboxylic acid, tert-butyl 7-[2-(4-nitrobenzyloxycarbonylamino)-2-phenylacetamido)]-3-(1-hydroxy-2-phenylethyl)-2-cephem-4-carboxylate, 4'-methoxybenzyl 7-(4-chlorophenoxyacetamido)-3-(1-hydroxypentyl)-2-cephem-4-carboxylate, benzhydryl 7-(2-thiazolylacetamido)-3-(1-hydroxyethyl)-2-cephem-4-carboxylate, dimethylallyl 7-propionamido-7-methoxy-3-(1-hydroxy-2-phenylethyl)-2-cephem-4-carboxylate, tert-butyl 7-(4-methoxyphenylacetamido)-3-(d-hydroxybenzyl)-2-cephem-4-carboxylate, benzhydryl 7-[2-(tert-butoxycarbonylamino)-2-(4-hydroxyphenyl)acetamido]-3-(1-hydroxyethyl)-2-cephem-4-carboxylate, and dimethylallyl 7-(3-thienylacetamido)-7-methoxy-3-(1-hydroxy-2-methylpropyl)-2-cephem-4-carboxylate.

The cephem γ-lactones derived from such exemplary carbinols are, likewise, illustrative of the biologically active cephem γ-lactones of the present invention available by procedures described hereinbefore.

The 7-acylamino-(7-methoxy)-2-cephems having a secondary carbinol functionality at C-3 are primarily useful as intermediates to the closely related cephem C-3 secondary acetates and C-3 acyl cephems of the present invention.

The 2-cephem C-3 secondary acetates are prepared by well known procedures from their respective secondary carbinols, such procedures comprising reacting the carbinol with either ketene or acetic anhydride in the presence of a tertiary amine base, e.g. pyridine, quinoline, triethylamine, N,N-diethylaniline and like bases. The reaction of cephem secondary carbinols with acetic anhydride in the presence of pyridine is a high yielding general reaction and thus is the preferred route to the 2-cephem secondary acetates of this invention.

The conversion of the 2-cephem secondary acetates to the corresponding 3-cephem derivatives is accomplished by an oxidation-reduction procedure well documented in the cephalosporin art. Generally, this procedure is carried out by first oxidizing the 2-cephem compound with, e.g. m-chloroperbenzoic acid, to give the corresponding 3-cephem 1-oxide derivative which is subsequently reduced to the 3-cephem by a trivalent phosphorous compound such as phosphorous trichloride or phosphorous tribromide, preferably employing dimethylformamide as the solvent for the reduction. Such a procedure is also employed for the conversion of the 3-acyl-2-cephem compounds of this invention described hereinbelow to the corresponding 3-acyl-3-cephems, preferred compounds of this invention. Application of the oxidation-reduction procedure to the above described secondary carbinols results primarily in lactone formation.

Removal of the C-4 carboxylic acid ester protecting group of the 3-cephem secondary acetates by employing conventional deesterification techniques, discussed in particular hereinbelow, provides antibiotic 7-acylamino-(7-methoxy)-3-[1-acetoxyalkyl or 1-acetoxyarylalkyl]-3-cephem-4-carboxylic acids of this invention, exemplary of which are the following:

7-(5-tetrazolylacetamido)-3-(1-acetoxyethyl)-3-cephem-4-carboxylic acid, 7-(2,5-dichlorophenylthioacetamido)-7-methoxy-3-(α-acetoxybenzyl)-3-cephem-4-carboxylic acid, 7-iodoacetamido-3-(1-acetoxypropyl)-3-cephem-4-carboxylic acid, 7-(3-chlorophenylacetamido)-3-(1-acetoxy-2-methylpropyl)-3-cephem-4-carboxylic acid, 7-(2-tert-butoxycarbonyl-2-phenylacetamido)-3-(1-acetoxy-2-phenylethyl)-3-cephem-4-carboxylic acid, and 7-phenoxyacetamido-7-methoxy-3-(1-acetoxybutyl)-3-cephem-4-carboxylic acid.

The 7-amino cephem secondary carbinols and acetate derivatives thereof are prepared, for example, from the corresponding C-7 4-nitrobenzyloxycarbonylamino cephem derivatives by cleavage of the carbamate moiety with a two-step procedure comprising hydrogenation in the presence of a palladium catalyst and subsequent cleavage of the reduced side chain under mildly acid conditions. The standard 7-acylamino $PCl_5$ cleavage procedures are not preferred because of the reactivity of the secondary carbinol functionality under such reaction conditions.

As stated hereinabove the 2-cephem compounds of this invention having a secondary carbinol functionality at C-3 are useful as intermediates to the corresponding 3-acyl compounds. The procedures by which the above described 2-cephem-3-secondary carbinols can be oxidized to the corresponding 3-acyl-2-cephem derivatives of this invention are identical to those described hereinabove for the preparation of the 3-formyl-2-cephem starting materials from the corresponding Δ²-desacetylcephalosporins. The use of "Jones Reagent" as the oxidizing agent, is preferred. Alternatively manganese dioxide can be utilized. U.S. Pat. No. 3,351,596 described the use of such oxidizing agents for the conversion of Δ³-desacetylcephalosporin esters to 3-formyl-3-cephem; the procedures described therein are equally applicable to the conversion of the above described 2-cephem C-3 secondary carbinols to their corresponding 3-acyl-2-cephem compounds. Generally, however, the oxidation of the secondary carbinols of this invention is carried out at a higher temperature than those temperatures described in the aforementioned patent. The oxidation of 2-cephem secondary carbinols to 3-acyl cephems is usually carried out at room temperature in an acetone medium by reacting the cephem secondary carbinol with a slight excess of Jones Reagent. After 15 to 30 minutes a volume of isopropanol is added to destroy any excess chromic acid. The product 3-acyl-2-cephem is isolated in high yield by using conventional isolation and purification techniques.

Alternatively oxidation of the cephem secondary carbinols can be carried out with excess manganese dioxide [activated by the method of Sondheimer et al., *J. Chem. Soc.*, 2189 (1953)] in refluxing chloroform.

The above described oxidations can be performed on 2-cephem secondary carbinols having either a carboxylic acid group or an ester protected carboxylic acid group at C-4. Preferably, if the oxidation is carried out on the free acid, the 3-acyl-2-cephem acid product is esterified before the double bond isomerization step to the 3-acyl-3-cephem compounds is carried out by the well-documented oxidation-reduction process briefly described hereinabove.

An alternative method for the preparation of the 3-acyl cephem derivatives of the present invention comprises reacting carbanionic reagents, such as Grignard reagents ($R_3MgX$), or alkyllithium reagents ($R_3Li$) at low temperature with a 3-carboxy cephem acid halide or mixed anhydride derivative of the formula

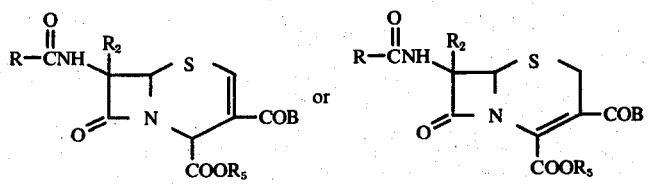

wherein R' and $R_5$ are as defined hereinabove and B is chloro or bromo or $C_2$–$C_5$ alkylcarbonyldioxy, including methylcarbonyldioxy, ethylcarbonyldioxy, isopropylcarbonyldioxy, isobutylcarbonyldioxy, sec-butylcarbonyldioxy or like lower alkylcarbonyldioxy groups. The reaction of carbanionic reagents with carboxylic acid mixed anhydride and acid chloride derivatives to provide ketones has been described in chemical literature [See e.g., Margaret J. Jorgenson, "Organic Reactions," Vol. 18, John Wiley and Sons, Inc., New York, N.Y., 1970, p. 1; G. H. Posner, C. E. Whitten and P. E. McFarland, *J. Amer. Chem. Soc.*, 94, 5106 (1972); G. H. Posner and C. E. Whitten, *Tetrahedron Letters*, 4647 (1970); Jacques-Emile Dubois, M. Boussu and C. Lion, *Tetrahedron Letters*, 829 (1971)]. Generally, however, for reasons stated hereinbefore, these carbanionic reagents have not been employed in such chemical conversions of cephem derivatives.

The following reaction scheme is illustrative of the preparation of 7-acylamino-3-acyl-3-cephems of this invention via 3-carboxy cephems:

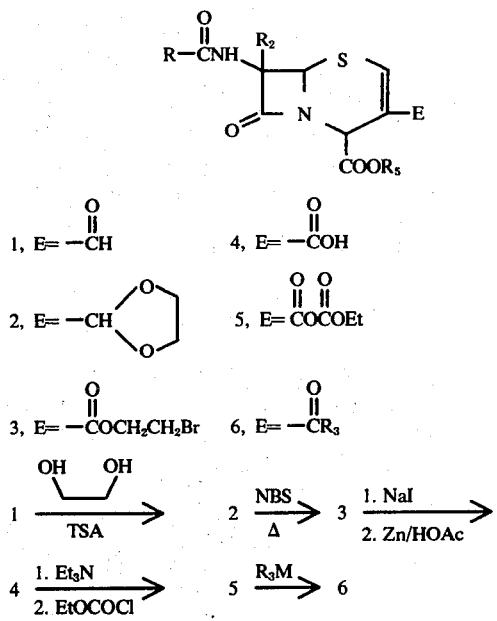

wherein in the above formulae R', $R_2$, $R_3$, and $R_5$ are as defined hereinabove.

The 3-formyl-2(or 3)-cephem starting material described hereinabove is first converted to its corresponding ethylene acetal derivative (2) preferably by reacting the 3-formyl derivative with a large excess of ethylene glycol in the presence of a catalytic amount of p-toluenesulfonic acid in refluxing benzene. Water is removed from the refluxing reaction mixture by the use of a Dean-Stark trap. After approximately 10 hours, or when water ceases to condense in the Dean-Stark trap, the reaction mixture is cooled and washed with sodium bicarbonate solution. The cyclic acetal thereby obtained is conveniently purified by chromatography over silica gel.

Oxidation of the ethylene acetal with N-bromosuccinimide in accordance with the procedures described by J. D. Prugh and W. D. McCarthy, *Tetrahedron Letters*, 1351 (1966) provides the corresponding 7-acylamino-3-(2-bromoethoxycarbonyl)-2(or 3) cephem-4-carboxylic acid ester (3). In general the acetaldiester conversion is carried out by reacting the acetal derivative with 1.0 to 1.2 molar equivalents of N- bromosuccinimide in the presence of a free radical initiator, such as azobisisobutyronitrile (AIBN) or benzoyl peroxide, in an inert organic solvent at a temperature between about 40° and 100° C.

The preferred conditions and procedures employed in the preparation of 7-acylamino-3-(2-bromoethoxycarbonyl)-2-cephem-4-carboxylic acid esters, intermediates to the compounds of this invention are summarily delineated in the following description of the preparation of 4'-nitrobenzyl 7-(2-thienylacetamido)-3-(2-bromoethoxycarbonyl)-3-cephem-4-carboxylate from the corresponding 3-formyl cephem ethylene acetal: A mixture of 5 mmol. of 4'-nitrobenzyl 7-(2-thienylacetamido)-3-(1,3-dioxolan-2-yl)-3-cephem-4-carboxylate, 5.5 mmol. of N-bromosuccinimide, and 0.05 mmol. of azobisisobutyronitrile in 200 ml. of benzene is heated to reflux for 20 to 25 minutes and then cooled and evaporated to dryness. Chromatography of the resultant product mixture on silica gel using a toluene-ethyl acetate gradient provides 4'-nitrobenzyl 7-(2-thienylacetamido)-3-(2-bromoethoxycarbonyl)-3-cephem-4-carboxylate.

The intermediate 7-acylamino-3-carboxy-2-cephem-4-carboxylic acid esters (4) and the corresponding 3-cephems are prepared by deesterification of 3-(2-bromoethoxycarbonyl) cephem derivatives. This deesterification is accomplished by a process comprising the conversion of the 2-bromoethyl ester group to the corresponding 2-iodoethyl ester, which group is subsequently removed reductively by treatment with 5 to 15 equivalents of zinc and excess acetic acid at 0°–5° C. The application of this two-step process for the removal of a 2-bromoalkyl ester group on cephalosporin compounds in particular has been described in Netherlands Pat. No. 7,010,475. The 2-iodoethyl esters are derived from the 2-bromoethyl esters by reaction with 1.5–4.0 equivalents of sodium iodide in acetone at 30°–40° C. for 15–20 hours. This is a known conversion (Finklestein reaction) and is accomplished in high yields with primary alkyl bromides such as the 2-bromoethyl ester group of the diester intermediates.

The deesterification of a 3-(2-bromoethoxycarbonyl) group of the hereinabove described 3,4-dicarboxycephem diester is, thus, preferably accomplished by (a) conversion to the corresponding 2-iodoethyl ester by reacting the diester with 3.0 equivalents of sodium iodide in acetone at 35° for 16 hours; and (b) reductive removal of the resultant iodoethyl group, e.g., by reaction with about 10 equivalents of zinc dust in a 1:6 mixture of acetic acid and dimethylformamide.

The mixed anhydride derivatives (5) are prepared from the 7-acylamino-3-carboxy-3(or 2)-cephem-4-carboxylic acid esters by known procedures. Generally the mixed anhydride derivatives are prepared by a two-step procedure comprising (a) treatment of the 3-carboxy cephem compounds with 1 equivalent of a tertiary amine, such as triethylamine, N-methylmorpholine, or N,N-diethylaniline, in an inert organic solvent at about −10° C. to 0° C. and (b) reacting the resulting tertiary amine salt with a $C_2$–$C_5$ alkylchloroformate such as methylchloroformate, ethylchloroformate, propylchloroformate, isobutylchloroformate or a like lower alkylchloroformate. Exemplary of the mixed anhydrides available by this procedure are:

benzhydryl 7-(2-thienylacetamido)-3-ethylcarbonyldioxycarbonyl-3-cephem-4-carboxylate,
4'-methoxybenzyl 7-(3-thienylacetamido)-3-methylcarbonyldioxycarbonyl-3-cephem-4-carboxylate,
tert-butyl 7-phenylacetamido-3-isobutylcarbonyldioxycarbonyl-3-cephem-4-carboxylate,
benzhydryl 7-phenoxyacetamido-3-ethylcarbonyldioxycarbonyl-3-cephem-4-carboxylate,
4'-methoxybenzyl 7-acetamido-3-methylcarbonyldioxycarbonyl-3-cephem-4-carboxylate,
benzhydryl 7-(2-thiazolylacetamido)-3-n-butylcarbonyldioxycarbonyl-3-cephem-4-carboxylate,
tert-butyl 7-(2,5-dichlorophenylthioacetamido)-3-ethylcarbonyldioxycarbonyl-3-cephem-4-carboxylate, and the corresponding 2-cephem compounds. These compounds can be isolated or reacted in situ with the desired nucleophilic reagents.

Acid halide derivatives of the 7-acylamino-3-carboxy-3(or 2)-cephem-4-carboxylic acid esters are prepared by the reaction of an appropriate halogenating agent with the sodium salt of the cephem acid. The sodium salts of the C-3 carboxylic acids are simply prepared by slurring a solution of the acid in ethyl acetate with an aqueous sodium bicarbonate solution. The sodium salt, being soluble in ethyl acetate, remains in the organic layer, which can be separated and dried by conventional drying agents such as anhydrous sodium sulfate, anhydrous magnesium sulfate or molecular sieves. The sodium salt can, thus, be isolated or can be reacted in the ethyl acetate solution with the desired halogenating reagent to give the acid halide derivative. Preferably, the sodium salt is isolated and dried thoroughly before it is employed in the acid halide preparation. Generally the acid chloride derivatives are prepared by reaction of the 7-acylamino-3-carboxylic acid-3(or 2)-cephem-4-carboxylic acid ester sodium salt with 2–3 equivalents of oxalyl chloride in methylene chloride in the presence of several drops of dimethylformamide at 0° to −5° C. The acid chloride derivative is then isolated by evaporation of the reaction mixture at low temperature to dryness; it is used without purification to prepare the hereinabove described 3-acyl cephem derivatives. Acid bromide derivatives are prepared by a similar method using phosphorous tribromide or thionyl bromide as the halogenating agent.

Illustrative of the acid halides which can be prepared by the above described procedures are:
benzhydryl 7-(2-thienylacetamido)-3-chlorocarbonyl-3-cephem-4-carboxylate,
benzhydryl 7-(4-tert-butoxycarbonyl-4-tert-butoxycarbamoylbutyl)-3-chlorocarbonyl-3-cephem-4-carboxylate,
tert-butyl 7-(4-methoxyphenylacetamido)-3-chlorocarbonyl-3-cephem-4-carboxylate,
4'-methoxybenzyl 7-iodoacetamido-3-chlorocarbonyl-3-cephem-4-carboxylate,
benzhydryl 7-(4-chlorophenylthioacetamido)-3-chlorocarbonyl-3-cephem-4-carboxylate,
tert-butyl 7-acetamido-3-chlorocarbonyl-3-cephem-4-carboxylate,
benzhydryl 7-(3-thienylacetamido)-3-chlorocarbonyl-3-cephem-4-carboxylate,
4'-methoxybenzyl 7-benzamido-3-chlorocarbonyl-3-cephem-4-carboxylate,
the corresponding 2-cephem compounds, and the corresponding 2-cephem and 3-cephem-3-bromocarbonyl compounds.

The final step of this alternative process for preparing the 3-acyl cephem compounds of this invention comprises the reaction of the aforedescribed 3-carboxy cephem derivatives with carbanionic reagents. Carbanionic reagents suitable for this conversion include Grignard reagents ($R_3MgX$) such as those illustrated hereinabove, and alkyl lithium reagents of the formula $R_3Li$, such as methyllithium isopropyl lithium, n-butyllithium, phenyllithium or benzyllithium.

The reaction of these carbanionic reagents with activated 3-carboxycephem intermediates (acid chlorides and mixed anhydrides) is carried out under the same conditions as discussed hereinabove for the process of this invention. A typical procedure is illustrated by reaction of benzhydryl 7-phenylacetamido-3-chlorocarbonyl-3-cephem-4-carboxylate with n-butyllithium. A ethereal solution of 3 equivalents of n-butyllithium is added to a solution of 1 mmole of benzhydryl 7-phenylacetamido-3-chlorocarbonyl-3-cephem-4-carboxylate in 30 ml. of tetrahydrofuran at −73° C. After approximately 5 minutes 10 ml. of 1N. hydrochloric acid is added, and the acidified mixture is then allowed to warm to about 0° C. Ethyl acetate is added, and the resulting mixture is washed with dilute hydrochloric acid and brine and dried over anhydrous sodium sulfate. Chromatographic purification provides benzhydryl 7-phenylacetamido-3-valeroyl-3-cephem-4-carboxylate.

Representative of the 3-acyl-3-cephem esters of this invention are:
dimethylallyl 7-(3-nitrobenzamido)-3-propionyl-3-cephem-4-carboxylate,
benzhydryl 7-[2-(4-nitrobenzyloxycarbonylamino)-2-(1,4-cyclohexadienyl)acetamido]-3-phenylacetyl-3-cephem-4-carboxylate,
tert-butyl 7-(3-furylacetamido)-3-(2-methylpropionyl)-3-cephem-4-carboxylate,
4'-methoxybenzyl 7-bromoacetamido-7-methoxy-3-benzoyl-3-cephem-4-carboxylate,
2'-iodoethyl 7-(4-methylphenylacetamido)-3-cyclohexylcarbonyl-3-cephem-4-carboxylate,
benzhydryl 7-(5-tetrazoylacetamido)-3-(2-methylbutyryl)-3-cephem-4-carboxylate,
benzhydryl 7-cyanoacetamido-3-propenoyl-3-cephem-4-carboxylate,
tert-butyl 7-(2-thienylacetamido)-3-valeryl-3-cephem-4-carboxylate, and
2'-iodoethyl 7-[2-benzyloxy-2-(4-hydroxyphenylacetamido)]-7-methoxy-3-benzoyl-3-cephem-4-carboxylate.

Grignard reagents react slowly with the aforedescribed 3-acyl-2-cephem esters under the reaction conditions of the process of the present invention to provide the biologically active γ-lactones of the present invention.

Because Grignard reagents react more slowly with the ketone derivatives than with the corresponding aldehydes, the reaction time is necessarily extended to approximately 45 minutes at about −75° C. There is no evidence of Grignard reagent attack on the β-lactam entity.

Representative of the biologically active cephem γ-lactones available from the reaction of Grignard reagents with the 3-acyl cephems of this invention are:
7-phenylacetamido-3-(1-hydroxy-1-methylpropyl)-3-cephem-4-carboxylic acid lactone,
7-acetamido-7-methoxy-3-(1-hydroxy-1-phenylethyl)-3-cephem-4-carboxylic acid lactone,
7-(2-furylacetamido)-3-(1-hydroxy-1-ethylpropyl)-3-cephem-4-carboxylic acid lactone,
7-[2-(2-carbomethoxyphenyl)acetamido]-3-(1-hydroxy-1-methylethyl)-3-cephem-4-carboxylic acid lactone, and
7-(3-bromophenoxyacetamido)-7-methoxy-3-(1-hydroxy-1-benzylpropyl)-3-cephem-4-carboxylic acid lactone.

The 7-acylamido(-7-methoxy)-3-acyl-3-cephem-4-carboxylic acid esters are converted to biologically active 7-acylamino(-7-methoxy)-3-acyl-3-cephem-4-carboxylic acids either directly, simply by cleavage of the C-4 carboxylic acid ester protecting group, or indirectly, by first modifying the 7-acylamino group before such deesterification.

The process for the preparation of the compounds of this invention can be carried out on starting materials having side chains most preferred for the preparative process (because of availability or stability to reaction conditions) and thereafter, such side chains can be cleaved and replaced by other 7-acylamino side chains preferred for maximum biological activity. The intermediate 7-amino (-7-methoxy)-3-acyl-3-cephem-4-carboxylic acid esters (or the corresponding 2-cephem compounds) are prepared by applying any of a variety of known amide cleavage procedures to the respective 7-acylamino compounds. For example, a 7-acylamino-3-acyl-3-cephem-4-carboxylic acid ester can be cleaved by the well known $PCl_5$/pyridine: alcohol:water procedure as described in U.S. Pat. No. 3,697,515. Alternatively, a nitrosyl chloride cleavage procedure described in U.S. Pat. 3,261,832 can be used. Other 7-acyl cleavage procedures for cephalosporin compounds are described, e.g. in U.S. Pat. Nos. 3,272,809 and 3,507,860. Alternatively, if the preparation of the 3-acyl cephems is carried out using cephems having a carbamate substitutent, e.g., 4-nitrobenzyloxycarbonylamino, at C-7, the respective amino esters may be prepared by cleavage of such carbamates via procedures documented in the art. Thus benzhydryl 7-(4-nitrobenzyloxycarbonylamino)-7-methoxy-3-benzoyl-3-cephem-4-carboxylate is converted to benzhydryl 7-amino-7-methoxy-3-benzoyl-3-cephem-4-carboxylate by a two-step procedure which comprises the mild reduction of the 4-nitrobenzyloxycarbonylamino group with hydrogen in the presence of a palladium catalyst to obtain an intermediate reduction product which is subsequently subjected to mildly acidic conditions to effect cleavage of the reduced side chain.

Exemplary of the nucleus esters of the present invention are:
benzhydryl 7-amino-3-propionyl-3-cephem-4-carboxylate,
tert-butyl 7-amino-7-methoxy-3-acetyl-3-cephem-4-carboxylate,
dimethylallyl 7-amino-3-(2-methylpropionyl)-3-cephem-4-carboxylate,
2'-iodoethyl-7-amino-3-phenylacetyl-2-cephem-4-carboxylate,
4'-methoxybenzyl 7-amino-7-methoxy-3-benzoyl-3-cephem-4-carboxylate,
benzhydryl 7-amino-3-butyryl-3-cephem-4-carboxylate,
4'-methoxybenzyl 7-amino-3-propenoyl-3-cephem-4-carboxylate,
tert-butyl 7-amino-3-cyclohexylcarbonyl-3-cephem-4-carboxylate,
dimethylallyl 7-amino-7-methoxy-3-acetyl-2-cephem-4-carboxylate, and benzhydryl 7-amino-3-phenylacetyl-3-cephem-4-carboxylate.

The corresponding 7-amino(-7-methoxy)-3-acetyl-3-cephem-4-carboxylic acids, nucleus acids of this invention, can be prepared either by deesterification of the above described amino esters or by C-7 carbamate cleavage of, for example, a 7-(4-nitrobenzyloxycarbonylamino)-3-acyl-3-cephem-4-carboxylic acid (prepared by deesterification of the corresponding ester). Removal of the C-4 carboxylic acid ester protecting group is discussed hereinbelow.

Exemplary of the nucleus acids of this invention are
7-amino-7-methoxy-3-acetyl-3-cephem-4-carboxylic acid,
7-amino-3-phenylacetyl-3-cephem-4-carboxylic acid,
7-amino-3-benzoyl-3-cephem-4-carboxylic acid,
7-amino-7-methoxy-3-(2-methylpropionyl)-3-cephem-4-carboxylic acid,
7-amino-3-butyryl-3-cephem-4-carboxylic acid, and
7-amino-3-(2-methylbutyryl)-3-cephem-4-carboxylic acid.

Such amino acids are isolated either as their zwitterions or, alternatively, as their acid addition or alkali metal salts depending on the pH of the medium from which they are isolated.

The nucleus acids and nucleus esters described hereinabove are useful intermediates for the preparation of those biologically active 7-acylamino-(7-methoxy)-3-acyl-3-cephem-4-carboxylic acids of the present invention which are preferred for antimicrobial activity.

Acylation of the nucleus acids or nucleus esters may be carried out by following known procedures used for the acylation of other cephalosporin nuclei, such as 7-ACA or 7-ADCA. For example, the nucleus ester can be reacted with an acyl halide, or a mixed anhydride derivative of the acid. Alternatively, and in accordance with known methods, a nucleus acid or ester can be acylated by its reaction with a carboxylic acid corresponding to the desired acyl group in the presence of a condensing agent such as dicyclohexylcarbodiimide or 2-ethoxy-N-ethoxycarbonyl-1,2-dihydroquinoline (EEDQ). The C-4 carboxylic acid ester protecting group of the acylated compounds thereby prepared is then removed by procedures described herein below. Either simultaneously, or subsequently, protecting groups of functionalities on the side chain, for example, the tert-butoxycarbonyl or 4-nitrobenzyloxycarbonyl employed in protecting an amino or hydroxy group, can be removed by procedures which are known to those skilled in the art.

Generally the nucleus acid derivatives can be acylated by methods which have been employed in the acylation of 6-APA, 7-ACA and 7-ADCA. One such method involves the addition of an acid chloride to a suspension of the amino acid and urea in acetone. Alternatively, the nucleus acid can be reacted with an acid anhydride derivative of the side chain acid in an inert anhydrous organic solvent such as acetone, ethyl acetate, methylene chloride or acetonitrile in the presence of a base, such as sodium bicarbonate, pyridine, triethylamine, N-methylmorpholine and the like. Furthermore, the amino acid derivative may be acylated to give the respective acylamino acid by first reacting the nucleus acid with a silylating agent, such as hexachlorodisilane, to form the corresponding silyl ester which is subsequently reacted with an active ester, for example, a pentachlorophenyl ester, of the acid corresponding to the desired side chain. A Schotten-Baumann type acylation may also be employed whereby the amino acid is reacted with the appropriate acid chloride in aqueous acetone in the presence of sodium bicarbonate.

Suitable acid chloride acylating agents which can be employed in preparing compounds of the present invention include phenylglycyl chloride hydrochloride, D-O-formylmandelic acid chloride, 2-phenyl-2-tert-butoxycarbonylacetyl chloride, D-2-(4-methoxyphenyl)-2-(4-nitrobenzyloxycarbonylamino)acetyl chloride, D-2-(4-hydroxyphenyl)-2-formyloxyacetyl chloride, (2,5-dichlorophenylthio)acetyl chloride, 2-(2-thienyl)-2-(tert-butoxycarbonylamino)acetyl chloride and like acid chlorides. Generally such compounds are prepared from their respective carboxylic acid salts via reaction with oxalyl chloride in an inert organic solvent in the presence of several drops of dimethylformamide.

Mixed anhydride reagents suitable for acylating the nucleus acids and nucleus diesters of the present invention include those which can be formed by the reaction of lower alkyl chloroformates, e.g. methyl chloroformate, ethyl chloroformate, or isobutyl chloroformate, and a sodium or tertiary amine salt of a carboxylic acid corresponding to the desired acyl substitutent. Representative of carboxylic acids from which such mixed anhydride acylating agents can be prepared are mandelic acid, 2-phenyl-2-tert-butoxycarbonylacetic acid, 2-hydroxyphenyl-2-(4-nitrobenzyloxycarbonylamino)acetic acid, N-tert-butoxycarbonylphenylglycine, 2-(2-thienyl)-2-(2,2,2-trichloroethoxycarboxyamino)acetic acid, 2-(4-hydroxyphenyl)-2-formyloxyacetic acid, and like carboxylic acid compounds.

Acylation of the nucleus acids provides preferred antibiotic compounds of this invention directly. Acylation of the nucleus esters provides preferred 7-acylamino-(7-methoxy)-3-acyl-3-cephem-4-carboxylic acid esters wherein the 7-acylamino group is selected for maximum biological activity.

Removal of the C-4 carboxylic acid ester protecting group of the 7-acylamino(-7-methoxy)-3-acyl-3-cephem-4-carboxylic acid esters provides preferred antimicrobial compounds of this invention. Cleavage of the ester moiety at C-4 to the free carboxyl function is achieved by conventional methods, the specific method employed being dependent upon the particular ester protecting group present. For example, the benzhydryl, tert-butyl, and 4-methoxybenzyl groups are readily removed by treatment with an acid such as trifluoroacetic acid, usually in the presence of a carbonium ion stabilizer such as anisole. The dimethylallyl ester protecting group is preferably removed by dissolution of the ester in formic acid at 0° C. Deesterification of the 2,2,2-trichloroethyl and 2-iodoethyl esters is accomplished by treatment with zinc and an acid such as formic acid, acetic acid or hydrochloric acid. Cleavage of the 4-nitrobenzyl ester protecting group is usually achieved by hydrogenating the ester in the presence of palladium, rhodium or the like in suspension or on a carrier such as barium sulfate, carbon, alumina or the like. It should be noted that these techniques can likewise be employed to remove like protecting groups, e.g. the corresponding oxycarbonyl hydroxy and amino protecting groups, which may be present elsewhere in the cephem compounds. Thus an amine function, protected with a tert-butoxycarbonyl group or a 4-methoxybenzylcarbonyl group can be deblocked by dissolution of the protected compound in a mixture of equal volumes of anisole and trifluoroacetic acid at 0° C. Benzhydryl 7-(2-tert-butoxycarbonyl-2-phenylacetamido)-3-acetyl-3-cephem-4-carboxylate is under similar conditions converted to 7-(2-carboxy-2-phenylacetamido)-3-acetyl-3-cephem-4-carboxylic acid.

Illustrative of preferred 7-acylamino(-7-methoxy)-3-acyl-3-cephem-4-carboxylic acids of the present invention are the following compounds:

7-(2-formyloxy-2-phenylacetamido)-3-acetyl-3-cephem-4-carboxylic acid,

7-[2-amino-2-(1,4-cyclohexadien-1-yl)acetamido]3-(3-butenoyl)-3-cephem-4-carboxylic acid, 7-(2-hydroxy-2-phenylacetamido)-3-benzoyl-3-cephem-4-carboxylic acid, 7-(2-carbomethoxy-2-phenylacetamido)-7-methoxy-3-propionyl-3-cephem-4-carboxylic acid, 7-[2-formyloxy-2-(4-hydroxyphenyl)acetamido]-3-(2-methylbutyryl)-3-cephem-4-carboxylic acid, 7-(2-benzyloxy-2-phenylacetamido)-7-methoxy-3-phenylacetyl-3-cephem-4-carboxylic acid, 7-(2-tert-butoxycarbonylamino-2-phenylacetamido)-3-(2-methylpropionyl)-3-cephem-4-carboxylic acid, 7-(2,5-dichlorophenylthiophenylacetamido)-7-methoxy-3-(3-butenoyl)-3-cephem-4-carboxylic acid, 7-[2-hydroxy-2-(4-methoxyphenyl)acetamido]-3-acetyl-3-cephem-4-carboxylic acid, 7-(2-carboxy-2-phenylacetamido)-7-methoxy-3-propionyl-3-cephem-4-carboxylic acid, 7-[2-amino-2-(2-thienyl)acetamido]-7-methoxy-3-valeryl-3-cephem-4-carboxylic acid, 7-(2-formyloxy-2-phenylacetamido)-7-methoxy-3-phenylacetyl-3-cephem-4-carboxylic acid, 7-[2-(4-nitrobenzyloxycarbonylamino)-2-(2-thienyl)-acetamido]-3-cyclohexylcarbonyl-3-cephem-4-carboxylic acid, 7-(2-tert-butoxycarbonyl-2-phenylacetamido)-3-acetyl-3-cephem-4-carboxylic acid, 7-[2-formyloxy-2-(4-chlorophenyl)acetamido)]-3-phenylacetyl-3-cephem-4-carboxylic acid, and 7-[2-hydroxy-2-(3-chloro-4-hydroxyphenyl)acetamido]-3-(2-methylpropionyl)-3-cephem-4-carboxylic acid.

The free acids of this invention form carboxylate salts with any of a variety or inorganic and organic bases. Pharmaceutically acceptable carboxylate salts are formed by reacting the free acids with bases such as sodium hydroxide, sodium carbonate, potassium hydroxide, potassium 2-ethylhexanoate, calcium carbonate, ethylamine, 2-hydroxyethylamine and like bases. Preferred carboxylate salt forms are the alkali metal salts. A preferred base for the formation of the potassium salt is potassium 2-ethylhexanoate. The carboxylate salts can be converted to the free acids by acidification. The free acids and their carboxylate salts can be considered as equivalent for the purpose of this invention.

The cephem antibiotics of this invention are relatively non-toxic substances which are useful in combatting infections in warm blooded mammals when administered parenterally in a pharmaceutically acceptable non-toxic dosage form. Furthermore, they can be formulated into liquid pharmaceutical form, e.g. in water, isotonic saline, or the like, and administered by intramuscular injections or by intravenous administration procedures to provide dosages of from about 125 mg. to 16 grams a day depending on the patient's body weight, the disease condition being treated, and other factors of concern to the patient's physician. In controlling infections in particular hosts, repeated administration of smaller doses may be administered to achieve the desired control. The antibiotic compounds of this invention can be administered in the free acid form or in the form of a pharmaceutically acceptable non-toxic salt, such as the sodium or potassium salt.

The following examples are provided to further illustrate this invention. It is not intended that this invention be limited in scope by reason of any of these examples. In the following examples, infrared absorption spectra and nuclear magnetic resonance spectra are abbreviated ir and nmr respectively. Only the ir absorptions attributable to the carbonyl function of the β-lactam ring and other significant functionalities giving rise to conspicuous ir absorptions are reported. The nuclear magnetic resonance spectra were obtained on a Varian Associated T-60 Spectrometer using tetramethylsilane as the reference standard. The chemical shifts are expressed in δ values in parts per million (ppm) and coupling constants (J) are expressed as Hz in cycles per second.

PREPARATION 1

Benzhydryl 7-(2-thienylacetamido)-3-formyl-2-cephem-4-carboxylate

To a slurry of 7-(2-thienylacetamido-3-hydroxymethyl-2-cephem-4-carboxylic acid (23.6 g., 67 mmol.) in 500 ml. ethyl acetate was added dropwise a solution of diphenyldiazomethane (19.4 g., 0.1 mole) in 50 ml. ethyl acetate. The reaction mixture was refluxed for 15 minutes, cooled to room temperature and evaporated in vacuo to dryness. The residue was washed with 1 liter of 1:1-ethyl ether:petroleum ether giving a pink solid:benzhydryl 7-(2-thienylacetamido)-3-hydroxymethyl-2-cephem-4-carboxylate (33 g., 94.2% yield).

To a stirred solution of the benzhydryl ester in 1 liter of acetone was added dropwise 33.6 ml. (76 mmol., 1.2 eq.) of chromic acid. The reaction mixture was allowed to stir at room temperature for 8 minutes. Isopropyl alcohol (35 ml.) was then added, and the mixture was stirred for an additional 5 minutes. The reaction mixture was evaporated in vacuo to low volume and extracted with ethyl acetate (2 × 400 ml.). The organic extracts were combined and washed successively with water (4X), sodium bicarbonate solution, water, 1N.HCl, and sodium chloride solution, and then dried ($Na_2SO_4$). Evaporation in vacuo to dryness gave 31.3 g. (95.4%) of crude benzhydryl 7-(2-thienylacetamido)-3-formyl-2-cephem-4-carboxylate which was purified either by crystallization from toluene (43% yield) or by chromatography on silica gel (50 g.) using a benzene-ethyl acetate gradient (22 g., 62% yield). The product was recrystallized from methylene chloride-hexane to give white needles (mp 149°–150° C.): ir ($CHCl_3$) 1785 (β-lactam C=O), 1680 (amide C=O) and 2830 cm$^{-1}$ (formyl C = ); nmr ($CDCl_3$) δ3.80 (s, 2, side chain $CH_2$), 5.12 (d, 1, J = 4.0 Hz, $C_6$—H), 5.40 (q, 1, J = 4.0 and 8.0 Hz, $C_7$—H), 5.51 (s, 1, $C_4$—H), and 9.20 (s, 1, CHO).

Analysis Calcd. for $C_{27}H_{22}N_2O_5S_2$: C, 62.53; H, 4.28; N, 5.40; Found: C, 62.33; H, 4.19; N, 5.17

PREPARATION 2

Benzhydryl 7-(2-thienylacetamido)-3-(1,3-dioxolan-2-yl)-2-cephem-4-carboxylate Benzhydryl 7-(2-thienylacetamido)-3-formyl-2-cephem-4-carboxylate (21.5 g., 41.5 mmol.) was combined with 11.6 ml. of ethylene glycol (0.2 mole) and toluenesulfonic acid monohydrate (0.197 g., 1.04 mmol.) in 500 ml. benzene. The mixture was refluxed for 10 hours using a Dean-Stark trap (1.5 ml. water collected), cooled, and evaporated in vacuo to dryness. The product was taken up in ethyl acetate and washed successively with sodium bicarbonate solution (2X), water (2X) and sodium chloride solution and subsequently dried over $Na_2SO_4$. Evaporation in vacuo to dryness gave a product which was chromatographed on 40 g. of silica gel using a benzene-ethyl acetate gradient. Crystallization of the purified product from methylene chloride-hexane gave benzhydryl 7-(2-thienylacetamido)-3-(1,3-dioxolan-2yl)-2-cephem-4-carboxylate as colorless needles (15.07 g., 64.2%: mp 142°–143°; ir ($CHCl_3$) 1780 $cm^{-1}$ ($\beta$-lactam C = O); nmr ($CDCl_3$) $\delta$3.3–3.9 (m, 4, —$CH_2$—$CH_2$), 3.83 (s, 2, side chain $CH_2$), 5.10 (d, 1, J=4.0 Hz, $C_6$—H), 5.17 (s, 1, acetal CH), 5.21 (s, 1, $C_4$—H) and 5.45 (q, 1, J=4.0 and 8.0 Hz, $C_7$—H).

Analysis Calcd. for $C_{29}H_{26}O_6S_2$: C, 61.69; H, 4.66; N, 4.98; Found: C, 61.69; H, 4.43; H, 5.10

PREPARATION 3

Benzhydryl 7-(2-thienylacetamido)-3-(2-bromoethoxycarbonyl)-2-cephem-4-carboxylate Benzhydryl 7-(2-thienylacetamido)-3-(1,3-dioxolan-2-yl)-2-cephem-4-carboxylate (15.07 g., 26.8 mmol.) was combined with N-bromosuccinimide (5.25 g., 29.5 mmol.) and azobisisobutyronitrile (36.5 mg., 0.26 mmol., 0.01 eq.) in 1200 ml. of benzene. The mixture was gently refluxed for 20 minutes, cooled, and evaporated in vacuo to dryness to give a dark colored product. Chromatography on 30 g. of silica gel using a toluene-ethyl acetate gradient provided 7.61 g. (44.4%) of benzhydryl 7-(2-thienylacetamido)-3-(2-bromoethoxycarbonyl)-2-cephem-4-carboxylate: mp 129°–130°; ir ($CHCl_3$) 1785 $cm^{-1}$ ($\beta$-lactum C = O); nmr ($CDCl_3$) $\delta$3.25 (t, 2, J = 6.0 Hz, $CH_2Br$), 3.83 (s, 2, side chain $CH_2$), 4.30 (t, 2, J = 6.0 Hz, O—$CH_2$—), 4.95 (d, 1, J = 4.0 Hz, $C_6$—H), 5.45 (q, 1, J = 4.0 and 8.0 Hz. $C_7$—H), 5.50 (s, 1, $C_4$—H) and 7.80 (s, 1, $C_2$—H).

Analysis Calcd. for $C_{29}H_{25}BrN_2O_6S_2$: C, 54.29; H, 3.93; N, 4.37; Found: C, 54.22; H, 3.90; N, 4.27

PREPARATION 4

Benzhydryl 7-(2-thienylacetamido)-3-(2-iodoethoxycarbonyl)-2-cephem-4-carboxylate Benzhydryl 7-(2-thienylacetamido)-3-(2-bromoethoxycarbonyl)-2-cephem-4-carboxylate (7.61 g., 12 mmol.) was combined with sodium iodide (6.75 g., 45 meq.) in 100 ml. acetone. The reaction mixture was degassed and then heated to 35° with stirring for 16 hours. The reaction mixture was filtered and evaporated to dryness. The residue was dissolved in ethyl acetate and washed with water (3X) and brine and dried ($Na_2SO_4$). Evaporation in vacuo to dryness provided 7.78 g. (95.5%) of benzhydryl 7-(2-thienylacetamido)-3-(2-iodoethoxycarbonyl)-2-cephem-4-carboxylate: ir ($CHCl_3$) 1785 $cm^{-1}$ ($\beta$-lactam C = O); nmr ($CDCl_2$) $\delta$ 2.96 (t, 2, J = 7.0 Hz, —$OCH_2$—), 3.80 (s, 2, side chain $CH_2$), 4.24 (t, 2, J = 7.0 Hz, —$OCH_2$—), 4.95 (d, 1, J=4.0 Hz, $C_6$—H), 5.24 (q, 1, J = 4.0 Hz, $C_7$—H, rest of the signal covered by $C_4$—H), 5.50 (s, 1, $C_4$—H), and 7.80 (s, 1, $C_2$—H).

PREPARATION 5

Benzhydryl 7-(2-thienylacetamido)-3-(2-bromoethoxycarbonyl)-3-cephem-4-carboxylate To a cooled (5° C.) stirred solution of benzhydryl 7-(2-thienylacetamido)-3-(2-bromoethoxycarbonyl)-2-cephem-4-carboxylate (0.29 g., 0.453 mmol.) in 30 ml. chloroform was added 85% m-chloroperbenzoic acid (0.101 g., .497 mmol.) in 3 ml. chloroform. The mixture was allowed to stir with cooling for 30 minutes, and then was washed with sodium bicarbonate solution (2X) and sodium chloride solution and dried over $Na_2SO_4$. Evaporation in vacuo gave 301 mg. of the $\Delta^3$ sulfoxide. The sulfoxide was dissolved in 25 ml. dimethylformamide, cooled briefly, and then treated with 0.06 ml. (0.678 mmol. 1.5 eq.) phosphorous trichloride. The mixture was allowed to stir at ambient temperature for 30 minutes. Ethyl acetate was added to the reaction mixture, and then it was washed successively with water (2X), aqueous sodium bicarbonate (2X) and brine. The organic layer was dried over anhydrous $Na_2SO_4$ and evaporated in vacuo to dryness. The crude product was chromatographed on 5 g. of silica gel using a benzene-ethyl acetate gradient providing benzhydryl 7-(2-thienylacetamido)-3-(2-bromoethoxycarbonyl)-3-cephem-4-carboxylate (0.154 g., 53%) as a colorless solid: ir ($CHCl_3$) 1799 $cm^{-1}$ ($\beta$-lactam C = O); nmr (DMSO-$d_6$) $\delta$3.34 (m, 2, $CH_2Br$), 3.76 (s, 2, side chain $CH_2$), 3.8–4.4 (m), 5.20 (d, 1, J = 5.0 Hz, $C_6$—H) and 5.86 (q, 1, J = 5.0 and 9.0 Hz, $C_7$—H).

PREPARATION 6

Benzhydryl 7-(2-thienylacetamido)-3-(2-iodoethoxycarbonyl)-3-cephem-4-carboxylate, 1-oxide To a cooled (ice bath 10 minutes), stirred solution of benzhydryl 7-(2-thienylacetamido)-3-(2-iodoethoxycarbonyl)-2-cephem-4-carboxylate (980 mg., 1.42 mmol.) in 70 ml. chloroform was added dropwise a solution of 85% m-chloroperbenzoic acid (0.319 g., 1.56 mmol.) in 5 ml. of chloroform. The mixture was allowed to stir overnight (11 hours) warming slowly to room temperature. The reaction mixture was washed successively with aqueous sodium bicarbonate (3X), water, and brine, dried over $Na_2SO_4$, and evaporated in vacuo to dryness. Chromatography on 5 g. of silica gel using a toluene-ethyl acetate gradient provided 0.219 g. of the starting material and 0.314 g. of benzhydryl 7-(2-thienylacetamido)-3-(2-iodoethoxycarbonyl)-3-cephem-4-carboxylate, 1-oxide (42% yield, corrected): nmr (DMSO-$d_6$) $\delta$3.03 (m, $CH_2I$), 3.8–4.3 (m, amide side chain $CH_2$, —$OCH_2$—, and $C_2$—H), 5.05 (d, J = 4.0 Hz, $C_6$—H) and 6.04 (q, 1, J = 4.0 and 8.0 Hz, $C_7$—H).

PREPARATION 7

Benzhydryl 7-(2-thienylacetamido)-3-(2-iodoethoxycarbonyl)-3-cephem-4-carboxylate To a cooled (ice bath 5 minutes), stirred solution of benzhydryl 7-(2-thienylacetamido)-3-(2-iodoethoxycarbonyl)-3-cephem-4-carboxylate, 1-oxide (0.314 g., 0.445 mmol.) in 20 ml. dimethylformamide was added 0.116 ml. phosphorous trichloride (1.34 mmol., 3.0 eq.). The ice bath was removed and the solution was stirred at room temperature for 45 minutes. Ethyl acetate was added to the reaction mixture, and the resulting mixture was washed with sodium bicarbonate solution (2X), water and brine and then dried over anhydrous $Na_2SO_4$. Evaporation of the solvent in vacuo provided a product which was subsequently chromatographed on silica using a toluene-ethyl acetate gradient to give benzhydryl 7-(2-thienylacetamido)-3-(2-iodoethoxycarbonyl)-3-cephem-4-carboxylate (0.207 g., 68%): nmr (DMSO-$d_6$) $\delta3.0$ (t, $CH_2$—I), 3.80 (s, 2, side chain $CH_2$), 3.6–4.2 (m, O—$CH_2$—), 5.25 ppm (d, 1, J = 5.0, $C_6$—H), and 5.80 (g, 1, J = 5.0 and 8.0 Hz, $C_7$—H).

PREPARATION 8

Benzhydryl 7-(2-thienylacetamido)-3-carboxy-2-cephem-4-carboxylate

Benzhydryl 7-(2-thienylacetamido)-3-(2-iodoethoxycarbonyl)-2-cephem-4-carboxylate (2.79 g., 4.05 mmol.) was dissolved in a mixture of 8 ml. of glacial acetic acid and 48 ml. dimethylformamide at 0° and was reacted with 2.79 g. zinc dust (10.5 eq.) for 1.5 hours. The reaction mixture was diluted with ethyl acetate and filtered through a celite filter. The filtrate was washed successively with sodium bicarbonate solution (3X), water, 1N.HCl, and brine and then dried ($Na_2SO_4$). Evaporation to dryness in vacuo gave 1.92 (89%) of benzhydryl 7-(2-thienylacetamido)-3-carboxy-2-cephem-4-carboxylate: nmr (CDCl$_3$) $\delta3.84$ (s, side chain $CH_2$), 4.99 (d, 1, J = 4.0 Hz, $C_6$—H), 5.45 (m, $C_4$—H and $C_7$—H) and 7.80 (s, $C_2$—H).

PREPARATION 9

Benzhydryl 7-(2-thienylacetamido)-3-ethylcarbonyldioxycarbonyl-2-cephem-4-carboxylate To a cooled (−10° C.), stirred solution of benzhydryl 7-(2-thienylacetamido)-3-carboxy-2-cephem-4-carboxylate (0.267 g., 0.5 mmol.) in 20 ml. methylene chloride under argon was added 0.051 g. triethylamine (0.5 mmol.). After stirring for several minutes at −10° C., the mixture was cooled to −20° and 0.162 g., (1.5 mmol.) ethyl chloroformate was added. The reaction mixture was allowed to stir at −20° for 30 minutes, and then allowed to warm to 0°. Cold ethyl acetate was added, and the resultant solution was washed successively with cold water, cold 1N.HCl, and cold brine and then dried ($Na_2SO_4$). Evaporation in vacuo to dryness gave 283 mg. (93.5%) of the mixed anhydride as a colorless froth: ir (CHCl$_3$) 1798 cm$^{-1}$ ($\beta$-lactam C = O); nmr (CDCl$_3$) $\delta1.34$ (t, 3, J = 7.0 Hz, $CH_2CH_3$), 3.80 (s, 1, side chain $CH_2$), 4.30 (q, 2, J = 7.0 Hz, $CH_2CH_3$), 5.02 (d, 1, J = 4.0 Hz, $C_6$—H), 5.40 (q, 1, 4.0 and 8.0 Hz, $C_7$—H), 5.55 (s, 1, $C_4$—H), and 4.72 (s, 1, $C_2$—H).

PREPARATION 10

7-(2-Thienylacetamido)-7-methoxy-3-acetoxymethyl-2-cephem-4-carboxylic acid.

To a cooled (0°), stirred solution of 7.75 g. of 7-(2-thienylacetamido)-7-methoxy-3-acetoxymethyl-3-cephem-4-carboxylic acid [prepared from cephalothin in accordance with procedures described by G. A. Koppel and R. E. Koehler, J. Amer. Chem. Soc., 95, 2403 (1973)] in 46 ml. of dry pyridine was added 5.02 ml. of acetic anhydride. The reaction mixture was allowed to stir with cooling for 2 hours, after which time the mixture was evaporated in vacuo to near dryness. The residue was dissolved in ethyl acetate, and the resulting solution was extracted 3 times with aqueous sodium bicarbonate. The aqueous extracts were combined, layered with ethyl acetate, and acidified with cold 1N.HCl. The organic layer was separated, washed with brine and dried over anhydrous sodium sulfate. Evaporation in vacuo to dryness provided 5.29 g. (68.2 percent) of the title product as a brown froth. Thin layer chromatography of the methyl ester derived from diazomethane exhibited a single spot. For identification purposes a small portion of the product acid was also converted to the corresponding benzhydryl ester using diphenyldiazomethane. Chromatography on a small silica gel column provided pure benzhydryl 7-(2-thienylacetamido)-7-methoxy-3-acetoxymethyl-2-cephem-4-carboxylate: ir (CHCl$_3$) 1780 cm$^{-1}$ ($\beta$-lactam); nmr (CDCl$_3$) $\delta1.92$ (s, 3, OAc), 3.42 (s, 3, OCH$_3$), 3.85 (s, 2, side chain $CH_2$), 4.55 (s, 2, —CH$_2$OAc), 5.01 (m, 1, $C_4$—H), 5.35 (s, 1, $C_6$—H) and 6.35 (m, 6, $CH_2$).

EXAMPLE 1

Benzhydryl 7-(2-thienylacetamido)-3-(1-hydroxyethyl)-2-cephem-4-carboxylate.

To a cooled (−73°), stirred solution of 5.19 g. of benzhydryl 7-(2-thienylacetamido)-3-formyl-2-cephem-4-carboxylate in 60 ml. of tetrahydrofuran under an argon atmosphere was added 10 ml. of a cold (−10°) 3 molar solution of methylmagnesium bromine in ethyl ether. The reaction mixture was stirred with cooling for 4 minutes after which time 10 ml. of 1N.HCl was added. The solution was then allowed to warm to 0° in an ice bath. The reaction mixture was transferred to separatory funnel with the aid of cold ethyl acetate and 1N.HCl. The organic layer was separated and washed with cold 1N.HCl (2X) and brine (2X), and dried over anhydrous sodium sulfate. Evaporation in vacuo to dryness gave a crude product which was chromatographed on silica gel using a toluene-ethyl acetate gradient to give 3.40 g. (63.9 percent) of the title product as a mixture of diastereoisomeric carbinols. Although both isomers have approximately the same rf value, careful fractionation of the column resulted in the isolation of the pure isomers. Isomer I (that which was eluded from the column first) crystallized from methylene chloride/hexane to provide white crystals (m.p. 133.5°–134.5°): ir (CHCl$_3$) 1782 cm$^{-1}$ (lactam C=O); nmr (CDCl$_3$) $\delta1.17$ (d, 3, J = 6.0 Hz,—CH(OH)CH$_3$), 2.85 (broad s, 1, —OH), 3.79 (s, 2, side chain CH$_2$), 4.27 (m, 1,—CH(OH)CH$_3$), 5.10 (s, 1, $C_4$—H), 5.13

(d, 1, J = 4.0 Hz, C₆—H), 5.49 (q, 1, J = 4.0 and 8.0 Hz, C₇—H) and 6.31 (s, 1, C₂—H).

Analysis Calcd. for $C_{28}H_{26}N_2O_5S_2$: C, 62.90; H, 4.90; N, 5.24; Found: C, 63.09; H, 5.01; N, 5.27.

The following physical chemical data was found for the amorphous isomer II of the title product: ir (CHCl₃) 1782 cm⁻¹ (lactam C = O); nmr (CDCl₃) δ1.15 (d, 3, J = 7.0 Hz,—CH(OH)CH₃), 2.72 (broad s, 1, —OH), 3.80 (s, 2, side chain CH₂), 4.27 (m, 1,—CH(OH)CH₃), 5.12 (d, 1, J = 4.0 Hz, C₆—H), 5.30 (s, 1, C₄—H), 5.49 (q, 1, J = 4.0 and 8.0 Hz, C₇—H), and 6.22 (s, 1, C₂—H).

Continued elution of the chromatographic column gave 0.176 g. (5 percent) of a rather polar material (2 spots on tlc) which crystallized in the collecting tubes and which was identified as the diastereoisomers of the cephem lactone resulting from the intramolecular cyclization of the C-3 hydroxyethyl group and the C-4 carboxylic acid ester functionality. Recrystallization from methylene chloride/hexane provided long white needles (mp 248°–249° decomp): nmr (CDCl₃) δ1.39 (d, J = 7.0 Hz, 3, —CH(OH)CH₃), 3.83 (s, 2, side chain CH₂), 5.10 (d, 1, J = 5.0 Hz, C₆—H), 5.31 (m, 1, J = 7.0 Hz, —CH(OH)CH₃), 5.86 (q, 1, J = 5.0 and 8.0 Hz, C₇—H).

EXAMPLE 2

Benzhydryl 7-(2-thienylacetamido)-3-acetyl-2-cephem-4-carboxylate.

To a stirred solution of 2.98 g. of benzhydryl 7-(2-thienylacetamido)-3-(1-hydroxyethyl)-2-cephem-4-carboxylate in 200 ml. of acetone was added dropwise 2.83 ml. of a 2.26 molar chromic acid solution. The reaction mixture was allowed to stir at room temperature for ten minutes, after which time approximately 10 ml. of isopropanol was added. The reaction mixture was stirred for 5 minutes and then evaporated in vacuo to dryness. The residue was taken up in a mixture of ethyl acetate and water and transferred to a separatory funnel with the aid of ethyl acetate. The organic layer was separated and washed successively with brine (4X), sodium bicarbonate solution, water, 1N.HCl, and brine (2X) and then dried over anhydrous sodium sulfate. The residue obtained upon evaporation in vacuo of the solution thereby obtained was chromatographed on a silica gel column using a toluene-ethyl acetate gradient to provide 2.11 g. (71.2 percent) of the title product:

nmr (CHCl₃) δ2.20 (s, 3,

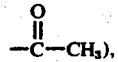

3.83 (s, 2, side chain CH₂), 4.98 (d, 1, J = 4.0 Hz, C₆—H), 5.47 (q, 1, J = 4.0 and 8.0 Hz, C₇—H), 5.60 (s, 1, C₄—H) and 7.54 (s, 1, C₂—H).

EXAMPLE 3

Benzhydryl 7-(2-thienylacetamido)-3-acetyl-3-cephem-4-carboxylate.

To a cooled (5° C.), stirred solution of 0.512 g. of benzhydryl 7-(2-thienylacetamido)-3-acetyl-2-cephem-4-carboxylate in 45 ml. of chloroform was added dropwise a solution of 0.215 g. of 85 percent m-chloroperbenzoic acid in 5 ml. of chloroform. The mixture was allowed to warm to room temperature. The reaction mixture was then washed with sodium bicarbonate solution (2X) and brine (2X) and dried over anhydrous sodium sulfate. Evaporation in vacuo of the dried chloroform solution gave a crude product which was purified by passing over a silica gel column using a toluene-ethyl acetate gradient. The purified intermediate 3-cephem sulfoxide (0.216 g., 41 percent) was dissolved in 20 ml. of dimethylformamide and after cooling the resulting solution briefly, was treated with 0.086 ml. of phosphorous trichloride. The mixture was allowed to stir at ambient temperature for 45 minutes. The dark brown solution was transferred to a separatory funnel with the aid of cold ethyl acetate, and was subsequently washed successively with cold sodium bicarbonate solution (2X), brine (3X), 1N.HCl and brine (2X), and then dried over anhydrous sodium sulfate. Evaporation in vacuo of the dried solution provided a crude product which was chromatographed on 5 g. of silica gel using a toluene-ethyl acetate gradient to give 0.146 g. (69.5 percent) of the title product as a white amorphous solid which crystallized as white needles from methylene chloride-acetone/hexane (m.p. 201°–202° decomp):

ir (CHCl₃) 1800 cm⁻¹ (lactam C = O); uv max (3A EtOH) 285 (ε 1.04 × 10⁴); nmr (DMSO d-6) δ2.18 (s, 3,

3.84 (broad s, 4, side chain CH₂ plus C₂—H), 5.23 (d, 1, J = 5.0 Hz, C₆—H), and 5.88 (q, 1, J = 5.0 and 8.0 Hz, C₇—H).

EXAMPLE 4

7-(2-Thienylacetamido)-3-acetyl-3-cephem-4-carboxylic acid.

To a cooled (5° C.) stirred slurry of 0.100 g. of benzhydryl 7-(2-thienylacetamido)-3-acetyl-3-cephem-4-carboxylate in 1 ml. of anisole was added 1 ml. of cold trifluoroacetic acid. The ester immediately dissolved. The resulting colorless solution was stirred with cooling for 20 minutes after which time approximately 40 ml. of n-heptane was added. The resulting solution was evaporated in vacuo to a low volume causing the precipitation of a white solid. The solid was filtered from the mixture and subsequently dissolved in acetone. The acetone solution was filtered and then evaporated in vacuo to dryness. The residue was dissolved in ethyl acetate, and the resulting solution was extracted three times with cold sodium bicarbonate solution. The aqueous extracts were combined, layered with ethyl acetate and acidified with 1N.HCl. The ethyl acetate layer was separated, washed with brine and dried over anhydrous sodium sulfate. Evaporation in vacuo to dryness gave 0.067 g. of the title product as a pale yellow solid which failed to crystallize from methylene chloride-hexane:

ir (CHCl₃) 1802 cm⁻¹ (lactam C = O); nmr (acetone d-6) δ1.74 (s, 3,

3.75 (s, 2, $C_2$—H), 3.82 (s, 2, side chain $CH_2$), 5.12 (d, 1, J = 5.0 Hz, $C_6$—H), 5.95 (q, 1, J = 5.0 and 8.0 Hz, $C_7$—H).

EXAMPLE 5

Benzhydryl 7-(2-thienylacetamido)-3-(1-acetoxyethyl)-2-cephem-4-carboxylate.

A. Ketene was bubbled for 16 minutes through a cooled (5° C.), stirred solution of 0.508 g. of benzhydryl 7-(2-thienylacetamido)-3-(1-hydroxyethyl)-3-cephem-4-carboxylate in 80 ml. of methylene chloride containing 5 drops of pyridine. The mixture was allowed to stir with cooling for 1.5 hours. The reaction mixture was then evaporated in vacuo to dryness. The residue was dissolved in ethyl acetate and the resulting solution was washed successively with cold 1N.HCl (2X), cold sodium bicarbonate solution, cold 1N.HCl, and brine (2X), and dried over anhydrous sodium sulfate. The residue obtained by evaporation of the solution to dryness was chromatographed on a silica gel column using a toluene-ethyl acetate gradient to give 0.501 g. (92 percent) of the title product as a yellow froth: ir ($CHCl_3$) 1784 $cm^{-1}$ (lactam C = O); nmr ($CDCl_3$) $\delta$1.20 (d, 3, J = 6.0 Hz,—CH(OAc)$CH_3$), 1.78 (s, 3, —OAc), 3.85 (s, 2, side chain $CH_2$), 5.0–5.7 (m, 4, $C_6$—H, $C_7$—H, $C_4$—H and —CH(OAc)$CH_3$), 6.45, 6.70 (broad peaks, $C_2$—H for the 2 different isomers).

B. A solution of 0.535 g. of benzhydryl 7-(2-thienylacetamido)-3-(1-hydroxyethyl)-2-cephem-4-carboxylate, 6 ml. of pyridine, and 2 ml. of acetic anhydride in 30 ml. of methylene chloride was refluxed at 42° C. for 2 hours. The reaction mixture was then evaporated in vacuo to dryness, and the resulting residue was dissolved in ethyl acetate and washed with 1N.HCl and brine, and dried over anhydrous sodium sulfate. Evaporation in vacuo of the dried solution to dryness provided 0.571 g. (99 percent) of the title product as a white froth. The product was identical to that prepared above via the reaction of ketene with the cephem carbinol.

EXAMPLE 6

Benzhydryl 7-(2-thienylacetamido)-3-(1-acetoxyethyl)-3-cephem-4-carboxylate 1-oxide.

To a cooled (5° C.), stirred solution of 0.897 g. of benzhydryl 7-(2-thienylacetamido)-3-(1-acetoxyethyl)-2-cephem-4-carboxylate in 80 ml. of chloroform was added a solution of 0.348 g. of 85 percent m-chloroperbenzoic acid in 3 ml. of chloroform. The reaction mixture was allowed to stir with cooling for 30 minutes after which time it was transferred to a separatory funnel with the aid of additional chloroform and washed successively with sodium bicarbonate solution (2X), and brine (2X) and dried over anhydrous sodium sulfate. The residue obtained by evaporation in vacuo to a froth which was chromatographed on a silica gel column using a toluene-ethyl acetate gradient to give 0.243 g. (26 percent) of what was labeled diastereoisomer I and 0.514 g. (55 percent) of what was labeled diastereoisomer II of the title product; isomer I coming off the column first.

Isomer I: ir ($CHCl_3$) 1805 $cm^{-1}$ (lactam C = O); nmr ($CDCl_3$) $\delta$1.34 (d, 3, J = 6.0 Hz,—CH(OAc)$CH_3$), 2.03 (s, 3, OAc), 3.00, 3.77 (ABq, 2, J = 18.0 Hz, $C_2$—H), 3.86 (s, 2, side chain $CH_2$), 4.35 (d, 1, J = 4.0 Hz, $C_6$—H), 5.8–6.3 (m, 2, $C_7$—H plus-CH—(OAc)$CH_3$).

Isomer II: ir ($CHCl_3$) 1805 $cm^{-1}$ (lactam C = O); nmr ($CDCl_3$) $\delta$1.17 (d, 3, J = 6.0 Hz,—CH(OAc)$CH_3$), 1.90 (s, 3, —OAc), 3.08, 3.70 (ABq, 2, J = 18.0 Hz, $C_2$—H), 3.80 (s, 2, side chain $CH_2$), 4.38 (1, d, J = 4.0 Hz, $C_6$—H), 5.8–6.3 (m, 2, $C_7$—H plus CH—(OAc)$CH_3$).

EXAMPLE 7

Benzhydryl 7-(2-thienylacetamido)-3-(1-acetoxyethyl)-3-cephem-4-carboxylate.

To a cooled solution of 0.514 g. of benzhydryl 7-(2-thienylacetamido)-3-(1-acetoxyethyl)-3-cephem-4-carboxylate 1-oxide (isomer II from the previous example) in 15 ml. of dimethylformamide was added 0.190 ml. of phosphorous trichloride. The reaction mixture was removed from the ice-bath and allowed to warm to room temperature at which temperature it was stirred for one hour. The reaction mixture was then transferred with the aid of ethyl acetate to a separatory funnel and was then washed with aqueous sodium bicarbonate solution (2X), and brine (2X) and then dried over anhydrous sodium sulfate. Evaporation in vacuo provided a product which was chromatographed on a silica gel column using a toluene-ethyl acetate gradient to give 0.328 g. (65.5 percent) of the title product as a froth: ir ($CHCl_3$) 1791 $cm^{-1}$ (lactam C = O); nmr ($CDCl_3$) $\delta$1.24 (3, d, J = 7.0 Hz,—CH(OAc)$CH_3$), 1.84 (s, 3, OAc), 3.36 (s, 2, $C_2$—H), 3.83 (s, 2, side chain $CH_2$), 4.93 (d, 1, J = 4.0 Hz, $C_6$—H), 5.72 (q, 1, J = 4.0 and 8.0 Hz, $C_7$—H), 6.20 (m, 1, J = 7.0 Hz,—CH-(OAc)$CH_3$).

A similar reduction of sulfoxide isomer II from the previous sample (isolated by chromatography) provided the corresponding sulfide: ir ($CHCl_3$) 1785 $cm^{-1}$ (lactam C = O); nmr ($CDCl_3$) $\delta$1.34 (d, 3, J = 6 Hz,—CH(OAc)$CH_3$), 1.97 (s, 3, —OAc), 3.34 (s, 2, $C_2$—H), 3.76 (s, 2, side chain $CH_2$), 4.85 (d, 1, J = 4.0Hz, $C_6$—H), 5.72 (q, 1, J = 4.0 and 8.0 Hz, $C_7$—H) and 6.0 (m, 1, CH(OAc)$CH_3$).

EXAMPLE 8

7-(2-Thienylacetamido)-3-(1-acetoxyethyl)-3-cephem-4-carboxylic acid.

To a cooled (5° C.), stirred solution of 0.328 g. of benzhydryl 7-(2-thienylacetamido)-3-(1-acetoxyethyl)-3-cephem-4-carboxylate in 1 ml. of anisole was added 1 ml. of cold trifluoroacetic acid. The reaction mixture was allowed to stir with cooling for 20 minutes after which time was added 30 ml. of n-heptane. The reaction mixture was evaporated in vacuo to a low volume, 20 ml. of n-heptane was added, and the resulting mixture was stirred with cooling for five minutes. The solid obtained by filtration of the resulting solution was dissolved in acetone, and the acetone solution was then filtered and evaporated to near dryness. The residue was dissolved in ethyl acetate, and the resulting solution was extracted three times with cold aqueous sodium bicarbonate solution. The aqueous extracts were combined, layered with ethyl acetate, and acidified with 1N.HCl. The organic layer was separated, washed with brine, and dried over anhydrous sodium sulfate. Evaporation in vacuo to dryness gave 94 mg. (40.5 percent) of the title product:

nmr (acetone D-6) δ1.44 (d, 3, J = 6.0 Hz,—CH-(OAc)CH$_3$), 2.17 (s, 3, —OAc), 3.62 (s, 2, C$_2$—H), 3.99 (s, 2, side chain CH$_2$), 5.00 (m, 3, C$_6$—H, C$_7$—H and —C$\underline{H}$(OAc)CH$_3$).

EXAMPLE 9

4'-Nitrobenzyl 7-(2-thienylacetamido)-3-acetyl-2-cephem-4-carboxylate.

To a cooled (5° C.), slurry of 0.535 g. of benzhydryl 7-(2-thienylacetamido)-3-acetyl-2-cephem-4-carboxylate in 1 ml. of anisole was added 1 ml. of cold trifluoroacetic acid. The reaction mixture was allowed to stir with cooling for 15 minutes after which time was added 30 ml. of n-heptane. The reaction mixture was evaporated in vacuo to a low volume and an additional 30 ml. of n-heptane was added. The resulting solution was stirred with cooling for 5 minutes and then filtered to provide a solid which was dissolved in acetone. The acetone solution was filtered, evaporated in vacuo to a low volume, and then transferred with the aid of ethyl acetate to a separatory funnel. The solution was extracted twice with cold aqueous sodium bicarbonate solution. The aqueous extracts were combined, layered with ethyl acetate, and acidified with 1N.HCl. The organic layer was separated, washed twice with brine, and then dried over anhydrous sodium sulfate. Evaporation in vacuo to dryness gave 0.337 g. of 7-(2-thienylacetamido)-3-acetyl-2-cephem-4-carboxylic acid as a white froth. To a solution of this product in ethyl acetate was added excess 4-nitrophenyldiazomethane. The reaction mixture was allowed to stir overnight at ambient temperature. The reaction mixture was evaporated in vacuo to dryness and the residue was chromatographed on a silica gel column using a toluene-ethyacetate gradient to give 0.229 g. (45.6 percent) of the title product which crystallized from methylene chloride/hexane as white needles (m.p. 149°–150°):
ir (CHCl$_3$) 1791 cm$^{-1}$ (lactam C = O); nmr (CDCl$_3$) δ2.28 (s, 3,

3.84 (s, 2, side chain CH$_2$), 5.10 (d, 1, J = 4.0 Hz, C$_6$—H), 5.28 (broad s, 2, ester CH$_2$), 5.50 (s, 1, C$_4$—H), 5.53 (q, 1, J = 4.0 and 8.0 Hz, C$_7$—H) and 7.70 (s, 1, C$_2$—H).

Analysis Calcd. for C$_{22}$H$_{19}$N$_3$O$_7$S$_2$: C, 52.69; H, 3.82; N, 8.38; Found: C, 52.97; H, 3.74; N, 8.45.

EXAMPLE 10

Benzhydryl 7-amino-3-acetyl-2-cephem-4-carboxylate.

Phosphorous pentachloride (0.478 g.) was added to a stirred solution of 1.065 g. of benzhydryl 7-(2-thienylacetamido)-3-acetyl-2-cephem-4-carboxylate and 0.199 ml. of pyridine in 9 ml. of methylene chloride. The reaction mixture was allowed to stir at room temperature for 2.5 hours. After cooling the mixture for 5 minutes in an ice bath, 0.985 ml. of isobutanol was added, and the reaction mixture was subsequently stirred at room temperature for one hour. The addition of n-hexane resulted in the formation of a brown solid from which the liquid was decanted. The residue was dissolved in an ethyl acetate-aqueous sodium bicarbonate slurry and transferred to a separatory funnel with the aid of ethyl acetate. The organic layer was separated and washed successively with aqueous sodium bicarbonate solution, water, and brine (2X), and dried over anhydrous sodium sulfate. Evaporation in vacuo to dryness provided a product which was chromatographed on a silica gel column using a toluene-ethyl acetate gradient to give a 0.521 g. (64 percent) of the title product as a tan froth:
ir (CHCl$_3$) 1782 cm$^{-1}$ (lactam C = O); nmr (CDCl$_3$) δ1.75 (s, 2, —NH$_2$), 2.17 (s, 3,

4.50 (d, 1, J = 4.0 Hz), 4.85 (d, 1, J = 4.0 Hz), 5.61 (s, 1, C$_4$—H), 6.87 (s, 1, ester CH), 7.4 (s, 10, ArH), and 7.69 (s, 1, C$_2$—H).

EXAMPLE 11

4'-Nitrobenzyl 7-amino-3-acetyl-2-cephem-4-carboxylate.

To a stirred slurry of 1.003 g. of 4'-nitrobenzyl 7-(2-thienylacetamido)-3-acetyl-2-cephem-4-carboxylate in 6 ml. of methylene chloride was added 0.199 ml. of pyridine and 0.478 g. of phosphorous pentachloride. The reaction mixture, under an argon atmosphere, was stirred at room temperature for 2.5 hours. After cooling the reaction mixture briefly in an ice bath 0.985 ml. of isobutanol was added. The reaction mixture was then stirred at room temperature for one hour. Addition of n-hexane resulted in the formation of purple crystals which were filtered and subsequently dissolved in a slurry of ethyl acetate and aqueous sodium bicarbonate solution. The organic layer was separated and washed with aqueous sodium bicarbonate solution and brine (2X) and then dried over anhydrous sodium sulfate. Evaporation in vacuo to dryness gave a residue which was chromatographed on a silica gel column using a toluene-ethyl acetate gradient to give 0.608 g. (80.5 percent) of the title product as a tan gum:
ir (CHCl$_3$) 1784 cm$^{-1}$ (lactam C = O); nmr (CDCl$_3$) δ2.00 (s, 2, —NH$_2$), 2.37 (s, 3,

4.79 (d, 1, J = 4.0 Hz), 5.15 (d, 1, J = 4.0 Hz), 7.90 (s, 1, C$_2$—H), and 7.60–8.30 (ArH).

EXAMPLE 12

Benzhydryl 7-amino-3-acetyl-3-cephem-4-carboxylate.

To a slurry of 0.457 g. of benzhydryl 7-(2-thienylacetamido)-3-acetyl-3-cephem-4-carboxylate in 5 ml. of methylene chloride was added .085 ml. of pyridine and 0.205 g. of phosphorous pentachloride. The reaction mixture was allowed to stir for two hours at room temperature. After cooling the reaction mixture briefly in an ice bath 0.425 ml. of isobutanol was added. After allowing the reaction mixture to stir at room temperature for one hour n-hexane was added dropwise causing a precipitate which, after cooling the reaction mixture briefly in an ice bath, was isolated by decanting the supernatant liquid. The product thereby isolated was dissolved in a slurry of ethyl acetate and aqueous sodium bicarbonate. The organic layer was separated, washed with aqueous sodium bicarbonate solution and brine and then dried over anhydrous sodium sulfate. Evaporation in vacuo to dryness provided 0.270 g. (77.9 percent) of title product as a brown froth:

ir (CHCl$_3$) 1795 cm$^{-1}$ (lactam C = O); nmr (CDCl$_3$) δ2.08 (s, 3,

2.45 (broad s, 2, —NH$_2$), 3.61 (m, 2, C$_2$—H), 4.85 (m, 2, C$_6$—H and C$_7$—H).

EXAMPLE 13

Benzhydryl 7-(2-formyloxy-2-phenylacetamido)-3-acetyl-3-cephem-4-carboxylate.

To a cooled (5° C.), stirred solution of 0.270 g. of benzhydryl 7-amino-3-acetyl-3-cephem-4-carboxylate in 20 ml. of dry tetrahydrofuran was added 0.0612 g. of sodium bicarbonate and dropwise, a solution of 0.144 g. of 2-formyloxy-2-phenylacetyl chloride in 2 ml. of tetrahydrofuran. The reaction mixture was allowed to stir with cooling for 30 minutes after which time it was transferred to a separatory funnel with the aid of cold ethyl acetate and washed with water, and brine (2X) and then dried over anhydrous sodium sulfate. Evaporation in vacuo to dryness provided a residue which was chromatographed on silica gel using a toluene-ethyl acetate gradient to give 0.194 g. (51.2 percent) of the title product as a white froth:

ir (CHCl$_3$) 1800 cm$^{-1}$ (lactam C = O); nmr (CDCl$_3$) δ2.02 (s, 3,

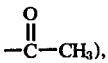

3.27, 3.53 (ABq, 2, J = 19.0 Hz, C$_2$—H), 4.86 (d, 1, J = 5.0 Hz, C$_6$—H), 5.80 (q, 1, J = 5.0 and 9.0 Hz, C$_7$—H), 6.22 (s, 1, side chain —CH), 7.00 (s, 1, benzhydryl CH), and 8.10 (s, 1, side chain —CHO).

EXAMPLE 14

7-(2-Formyloxy-2-phenylacetamido)-3-acetyl-3-cephem-4-carboxylic acid.

To a cooled (5° C.), stirred slurry of 0.194 g. of benzhydryl 7-(2-formyloxy-2-phenylacetamido)-3-acetyl-3-cephem-4-carboxylate in 10 ml. of anisole was added 1 ml. of cold trifluoroacetic acid. After allowing the reaction mixture to stir with cooling for 15 minutes, 30 ml. of n-heptane was added and the resulting solution was evaporated in vacuo to a low volume. An additional 30 ml. of n-heptane was added, and the resulting solution was stirred with cooling in an ice bath for 5 minutes. The solid obtained by filtration of the n-heptane solution was dissolved in acetone, the acetone solution was filtered, and the filtrate was evaporated in vacuo to a low volume. The residue was transferred with the aid of cold ethyl acetate to a separatory funnel where the resulting ethyl acetate solution was extracted twice with cold aqueous sodium bicarbonate solution. The aqueous extracts were combined, layered with cold ethyl acetate, and acidified with cold 1N.HCl. The organic layer was separated, washed twice with brine, and dried over anhydrous sodium sulfate. Evaporation in vacuo to dryness provided 0.136 g. (99.3 percent) of the title product as a white froth which failed to crystallize from acetone/hexane or chloroform/hexane:

ir (CHCl$_3$) 1805 cm$^{-1}$ (lactam C = O); nmr (CDCl$_3$) δ1.70 (s, 3,

3.70 (s, 2, C$_2$—H), 5.06 (d, 1, J = 5.0 Hz, C$_6$—H), 5.92 (q, 1, J = 5.0 and 8.0 Hz, C$_7$—H), 6.30 (s, 1, side chain —CH), 7.6 (10, ArH), and 8.40 (s, 1, —CHO).

EXAMPLE 15

4′-Nitrobenzyl 7-(2-tert-butoxycarbonylamino-2-phenylacetamido)-3-acetyl-2-cephem-4-carboxylate.

To a cooled (−20° C.) stirred solution of 0.485 g. of 2-tert-butoxycarbonylamino-2-phenylacetic acid and 30 ml. of tetrahydrofuran under an argon atmosphere was added 0.212 ml. of N-methylmorpholine and subsequently 0.174 ml. of 97 percent methyl chloroformate. This mixture was allowed to stir at −20° for 10 minutes. Subsequently the mixture was cooled to a −30° C, and then a solution of 0.608 g. of 4′-nitrobenzyl 7-amino-3-acetyl-2-cephem-4-carboxylate in 8 ml. of tetrahydrofuran was added dropwise to the mixture. The reaction mixture was allowed to stir at −25° to −5° over a 30 minute period. The reaction mixture was transferred to a separatory funnel with the aid of cold ethyl acetate and was washed successively with cold 1N.HCl, cold aqueous sodium bicarbonate solution, and brine and then dried over anhydrous sodium sulfate. Evaporation in vacuo provided a product which was purified by chromatography on silica gel using a toluene-ethyl acetate gradient to provide 0.305 g. (63 percent) of the title product as a white froth:

ir (CHCl$_3$) 1793 cm$^{-1}$ (lactam C = O); nmr (CDCl$_3$) δ1.44 (s, 9, tert-butyl), 2.27 (s, 3,

5.15 (d, 1, J = 4.0 Hz, C$_6$—H), 5.33 (s, 2, ester CH$_2$), 5.59 (s, 1, C$_4$—H), 5.66 (q, 1, J = 4.0 and 8.0 Hz, C$_7$—H), 5.96 (d, 1, J = 6.0 Hz, side chain CH), 7.5 (5, ArH), 7.6–8.3 (m, 4, ester ArH), and 7.65 (s, 1, C$_2$—H).

EXAMPLE 16

Benzhydryl 7-[2-(1-carbomethoxy-2-propenylamino)-2-phenylacetamido]-3-acetyl-2-cephem-4-carboxylate.

To a cooled (−15° C.), stirred slurry of 0.381 g. of 2-(1-carbomethoxy-2-propenylamino)-2-phenylacetic acid and 25 ml. of tetrahydrofuran was added three drops of N,N-dimethylbenzylamine and 0.109 ml. of methyl chloroformate. The reaction mixture was allowed to stir with cooling under an argon atmosphere for 10 minutes. The reaction mixture was then cooled to −20° C. and a solution of 0.521 g. of benzhydryl 7-amino-3-acetyl-2-cephem-4-carboxylate in 5 ml. of tetrahydrofuran was added dropwise. The resulting mixture was allowed to stir under argon with cooling for approximately one hour, after which time the mixture was transferred to a separatory funnel with the aid of cold ethyl acetate. The organic solution was washed with cold 1N.HCl, and brine, and then dried over anhydrous sodium sulfate. Evaporation in vacuo to dryness gave a product which was chromatographed on silica gel using a toluene-ethyl acetate gradient to give 0.556 g. (68 percent) of the title product as a tan froth: nmr (CDCl₃) δ1.79 (s, 3, vinylmethyl), 2.17 (s, 3,

3.63 (s, 5, side chain CH₂ plus — OCH₃), 2.75 (s, 1), and 4.90 (d, 1, J = 4.0 Hz, C₆—H).

EXAMPLE 17

Benzhydryl 7-(2-thienylacetamido)-3-(1-hydroxypropyl)-2-cephem-4-carboxylate.

To a cooled (−73° C.), stirred solution of 1.559 g. of benzhydryl 7-(2-thienylacetamido)-3-formyl-2-cephem-4-carboxylate and 20 ml. of dry tetrahydrofuran was added 3.13 ml. of 2.88 M. ethyl magnesium bromide. After the reaction mixture was allowed to stir for four minutes at −73° C., 10 ml. of 1N.HCl was added and the solution allowed to warm to 0° C. The reaction mixture was transferred to a separatory funnel with the aid of cold ethyl acetate and cold 1N.HCl. The organic layer was separated and washed twice with cold 1N.HCl and twice with brine and then dried over anhydrous sodium sulfate. Evaporation in vacuo to dryness provided a product residue which was chromatographed on silica gel using a toluene-ethyl acetate gradient to give 0.140 g. of the starting 3-formyl-2-cephem ester and 0.507 g. (30.6 percent) of the title product as a mixture of diasteromers:
ir (CHCl₃) 1783 cm⁻¹ (lactam C = O); nmr (CDCl₃) δ0.80 (m, J = 6.0 Hz, 3, —CH₂C$\underline{H}$₃), 1.47 (m, 2, —C$\underline{H}$₂CH₃), 2.50 (m, 1, —OH), 3.85 (s, 2, side chain CH₂), 3.96 (m, 1, —CH(O$\underline{H}$)Et), 5.14 (1, C₆—H), 5.20 (broad s, 1, C₄—H), 5.55 (q, 1, J = 5.0 and 8.0 Hz, C₇—H), 6.20 and 6.30 (s, 1, C₂—H) of each isomer).

EXAMPLE 18

Benzhydryl 7-(2-thienylacetamido)-3-propionyl-2-cepham-4-carboxylate.

To a stirred solution of 0.507 g. of benzhydryl 7-(2-thienylacetamido)-3-(1-hydroxypropyl)-2-cephem-4-carboxylate and 40 ml. of acetone was added dropwise 0.47 ml. of a 2.26 molar solution of chromic acid. After allowing the reaction mixture to stir for 10 minutes at room temperature, 10 ml. of isopropanol was added to the green solution. The reaction mixture was evaporated in vacuo to dryness, dissolved in an ethyl acetate/water slurry, and transferred to a separatory funnel with the aid of ethyl acetate. The organic layer was separated and washed four times with brine and then dried over anhydrous sodium sulfate. Chromatography of the residue, obtained by evaporating the solution in vacuo to dryness, over a silica gel column using a toluene-ethyl acetate gradient provided 0.290 g. (57.5 percent) of the title product as a white froth which failed to crystallize from methylene chloride/hexane overnight:
ir (CHCl₃) 1787 cm⁻¹ (lactam C = O); nmr (CDCl₃) δ1.01 (t, 3, J = 8.0 Hz, —CH₂C$\underline{H}$₃), 2.45 (q, 2, J = 8.0 Hz, —C$\underline{H}$₂CH₃), 3.84 (s, 2, side chain CH₂), 5.00 (d, 1, J = 4.0 Hz, C₆—H), 5.42 (q, 1, J = 4.0 and 8.0 Hz, C₇—H), 5.65 (s, 1, C₄—H), and 7.52 (s, 1, C₂—H).

EXAMPLE 19

Benzhydryl 7-(2-thienylacetamido)-3-propionyl-3-cephem-4-carboxylate.

To a cooled (5° C.), stirred solution of 0.363 g. of benzhydryl 7-(2-thienylacetamido)-3-propionyl-2-cephem-4-carboxylate in 30 ml. of chloroform was added dropwise a solution of 0.149 g. of 85 percent m-chloroperbenzoic acid in 3 ml. of chloroform. The reaction was allowed to stir with cooling for one hour, after which time it was washed twice with aqueous sodium bicarbonate solution and twice with brine and then dried over anhydrous sodium sulfate. The solution was then evaporated in vacuo to provide a gel which was dissolved in 15 ml. of dimethylformamide. This solution was cooled for five minutes in an ice bath, removed from the ice bath, and subsequently treated with 0.145 ml. of phosphorous trichloride. This mixture was allowed to stir at room temperature for 45 minutes, after which time it was transferred to a separatory funnel with the aid of ethyl acetate and washed successively with aqueous sodium bicarbonate (2X), water (4X), and brine (2X) and then dried over anhydrous sodium sulfate. Evaporation in vacuo to dryness gave a product which when chromatographed on silica gel using a toluene-ethyl acetate gradient provided 0.267 g. (74 percent) of the title product as a white solid which crystallized as white needles from methylene chloride/hexane (m.p. 220°–221° decomp.): nmr (DMSO d-6) δ0.80 (t, 3, J = 7.0 Hz, —CH₂C$\underline{H}$₃), 2.5 (m), 3.84 (s, 2, side chain CH₂), 5.22 (d, 1, J = 4.0 Hz, C₆—H), 5.92 (q, 1, J = 4.0 and 8.0 Hz, C₇—H).

Analysis Calcd. for: C₂₉H₂₆N₂O₅S₂: C, 63.72; H, 4.79; N, 5.12; Found: C, 63.65; H, 5.09; N, 5.37.

EXAMPLE 20

7-(2-Thienylacetamido)-3-propionyl-3-cephem-4-carboxylic acid.

To a cooled (5° C.), stirred slurry of 0.168 g. of benzhydryl 7-(2-thienylacetamido)-3-propionyl-3-cephem-4-carboxylate in 2 ml. of anisole was added 1 ml. of cold trifluoroacetic acid. The reaction mixture was allowed to stir with cooling for 20 minutes after which time 30 ml. of n-heptane was added. After the resulting solution was evaporated in vacuo to a low volume to remove excess trifluoroacetic acid, an additional 30 ml. of n-heptane was added. After stirring the reaction mixture in an ice bath for five minutes the mixture was filtered. The solid was dissolved in acetone, and the acetone solution was filtered. The filtrate was evaporated to low volume and subsequently transferred to a separatory funnel with the aid of cold ethyl acetate. The ethyl acetate solution was extracted twice with cold aqueous sodium bicarbonate solution. The aqueous extracts were combined, layered with cold ethyl acetate, and acidified with cold 1N.HCl. The organic layer was separated and washed twice with brine and dried over anhydrous sodium sulfate. Evaporation in vacuo to dryness provided 0.108 g. (92 percent) of the title product as a white solid:
ir (CHCl$_3$) 1801 cm$^{-1}$ (lactam C = O); nmr (acetone d-6) δ0.88 (t, 3, —CH$_2$CH$_3$), 2.09 (m), 3.75 (s, 2, C$_2$—H), 4.00 (s, 2, side chain CH$_2$), 5.22 (d, 1, J = 4.0 Hz, C$_6$—H), 6.00 (q, 1, J = 4.0 and 6.0 Hz, C$_7$—H) and 6.45 (broad s, 1, COOH).

EXAMPLE 21

Benzhydryl 7-(2-thienylacetamido)-3-benzoyl-2-cephem-4-carboxylate.

To a cooled (−73° C.), stirred solution of 1.04 g. of benzhydryl 7-(2-thienylacetamido)-3-formyl-2-cephem-4-carboxylate and 8 ml. of tetrahydrofuran was added 2.4 ml. of a 2.5 molar phenylmagnesium bromide solution. After stirring the reaction mixture with cooling for four minutes, 8 ml. of 1N.HCl was added, and the reaction mixture was allowed to warm to 0°. Ethyl acetate was added, and the reaction mixture was then washed twice with cold 1N.HCl, and twice with brine and then dried over anhydrous sodium sulfate. Evaporation in vacuo to dryness gave a residue which was chromatographed on a silica gel column using a toluene-ethyl acetate gradient. This chromatography failed to separate the unreacted starting material (3-formyl-2-cephem ester) and the product cephem secondary carbinol. Combining the fractions off the column and evaporating in vacuo to dryness gave 0.895 g. of a mixture which was dissolved in 50 ml. of acetone and reacted with 0.77 ml. of a 2.26 molar solution of chromic acid. This reaction mixture was allowed to stir for 15 minutes at room temperature after which time 5 ml. of isopropanol was added. After five minutes the reaction mixture was evaporated in vacuo to dryness, and the residue was dissolved in an ethyl acetate/water slurry and then transferred to a separatory funnel with the aid of ethyl acetate. The organic layer was separated and washed with water (4X) and brine (2X) and then dried over anhydrous sodium sulfate. Evaporation in vacuo to dryness and chromatography of the residue thereby obtained on silica using a toluene-ethyl acetate gradient provided 0.213 g. of the 3-formyl-2-cephem starting material and 0.366 g. (41 percent) of the title product which crystallized from methylene chloride hexane as white needles (m.p. 179°–180°):
nmr (DMSO d-6) δ3.84 (s, 2, side chain CH$_2$), 5.27 (d, 1, J = 4.0 Hz, C$_6$—H), 5.62 (q, 1, J = 4.0 and 8.0 Hz, C$_7$—H), 5.92 (s, 1, C$_4$—H), and 7.80 (s, 1, C$_2$—H).
Analysis Calcd. for C$_{33}$H$_{26}$N$_2$O$_5$S$_2$: C, 66.65; H, 4.41; N, 4.71; Found: C, 66.46; H, 4.24; N, 4.55.

EXAMPLE 22

Benzhydryl 7-(2-thienylacetamido)-3-benzoyl-3-cephem-4-carboxylate.

A solution of 0.385 g. of m-chloroperbenzoic acid in 5 ml. of methylene chloride was added dropwise over a 10 minute period to a cooled (5° C.), stirred solution of 1.023 g. benzhydryl 7-(2-thienylacetamido)-3-benzoyl-2-cephem-4-carboxylate in 50 ml. of methylene chloride. After two hours the reaction mixture was washed with sodium bicarbonate solution (3X), and brine, dried over anhydrous sodium sulfate and evaporated in vacuo to dryness to provide the corresponding 3-cephem sulfoxide. The product sulfoxide was dissolved in 20 ml. of dimethylformamide (cooled in an ice bath) and was treated with 0.374 ml. of phosphorous trichloride. The mixture was removed from the ice bath and allowed to react at room temperature for 45 minutes. Ethyl acetate was added to the reaction mixture, and the resulting solution was washed successively with aqueous sodium bicarbonate solution, water (4X), and brine (2X), and dried over anhydrous sodium sulfate. The solution was evaporated in vacuo to dryness. The product was chromatographed on a silica gel column using a toluene-ethyl acetate gradient to provide 0.528 g. (52 percent) of the title product as a white solid which crystallized as white needles from methylene chloride/hexane (m.p. 209°–210° decomp.):
ir (CHCl$_3$) 1800 cm$^{-1}$ (lactam C = O); nmr (DMSO D-6) δ3.84 (s, 4, side chain CH$_2$ plus C$_2$—H), 5.45 (d, 1, J = 5.0 Hz, C$_6$—H) and 6.00 (q, 1, J = 5.0 and 8.0 Hz, C$_7$—H).
Analysis Calcd. for C$_{33}$H$_{26}$N$_2$O$_5$S$_2$: C, 66.65; H, 4.41; N, 4.71; Found: C, 66.87; H, 4.70; N, 4.76.

EXAMPLE 23

7-(2-Thienylacetamido)-3-benzoyl-3-cephem-4-carboxylic acid.

To a cooled (5° C.), stirred slurry of 0.227 g. of benzhydryl 7-(2-thienylacetamido)-3-benzoyl-3-cephem-4-carboxylate in 2 ml. of anisole was added 1 ml. of cold trifluoroacetic acid. After the reaction mixture was allowed to stir with cooling for 20 minutes, 20 ml. of n-heptane was added, and the resulting solution was evaporated in vacuo to a low volume to remove excess trifluoroacetic acid. An additional 20 ml. of n-heptane was added to the residue and the resulting solution was stirred with cooling for approximately 5 minutes. The white precipitate which formed was filtered from the solution and dissolved in acetone. The acetone solution was filtered and the filtrate evaporated in vacuo to a low volume. The residue was dissolved in cold ethyl acetate and transferred to a separatory funnel. The ethyl acetate solution was extracted twice with cold aqueous sodium bicarbonate solution. The aqueous extracts were combined, layered with cold ethyl acetate and acidified with cold 1N.HCl. The ethyl acetate layer was separated, washed twice with brine, and dried over anhydrous sodium sulfate. Evaporation in vacuo to dryness provided 0.157 g. (96 percent) of the title acid which crystallized from methylene chloride/hexane. The product exhibited activity against gram-positive and gram-negative organisms at 0.1 mg/ml in a standard disc assay.

EXAMPLE 24

7-(2-Thienylacetamido)-3-(1-methyl-1-hydroxyethyl)-3-cephem-4-carboxylic acid lactone.

To a cooled (−75° C.), stirred solution of 0.419 g. of benzhydryl 7-(2-thienylacetamido)-3-acetyl-2-cephem-4-carboxylate in 6 ml. of dry tetrahydrofuran under argon was added 0.80 ml. of cold 3.0 molar methylmagnesium bromide in tetrahydrofuran. After allowing the reaction mixture to stir with cooling for 45 minutes, 2 ml. of 1N.HCl was added and the reaction mixture was allowed to warm to 0° C. The mixture was then transferred to a separatory funnel with the aid of cold ethyl acetate. The mixture was then washed successively with 1N.HCl (cold), water, and brine and then dried over anhydrous sodium sulfate. Evaporation in vacuo to dryness gave a residue which was chromatographed on 5.0 g. of silica gel using a toluene-ethyl acetate gradient to give 0.211 g. of the starting ketone and 0.037 g. (13 percent) of the title lactone as a white crystalline solid. The lactone was recrystallized from methylene chloride/acetone/hexane to give white needles (m.p. 230°–235° decomp):
nmr (DMSO d-6) δ1.48 (s, 3, CH$_3$), 3.78 (s, 4, side chain CH$_2$ plus C$_2$—H), 5.08 (d, 1, J = 4.0 Hz, C$_6$—H), and 5.80 (q, 1, J = 4.0 and 8.0 Hz, C$_7$—H).

Analysis Calcd. for C$_{16}$H$_{16}$N$_2$O$_4$S$_2$: C, 52.73; H, 4.43; N, 7.69; Found: C, 52.96; H, 4.53; N, 7.94.

EXAMPLE 25

Benzhydryl 7-(2-thienylacetamido)-7-methoxy-3-formyl-2-cephem-4-carboxylate.

To a solution of 1.34 g. of 7-(2-thienylacetamido)-7-methoxy-3-acetoxymethyl-2-cephem-4-carboxylic acid in 4 ml. of acetone and 40 ml. of water was added 6.3 ml. of 1N.NaOH. The resulting brown solution was stirred at 45° C. for 15 hours. [Procedure of Cocker et al., J. Chem. Soc., 1142 (1966)]. The mixture was then cooled to room temperature, layered with ethyl acetate and acidified with cold 1N.HCl. The aqueous layer was separated and again extracted with ethyl acetate. The ethyl acetate extracts were combined, washed twice with brine and dried over anhydrous sodium sulfate. Evaporation in vacuo to dryness gave 1.06 g. (87.5 percent) of 7-(2-thienylacetamido)-7-methoxy-3-hydroxymethyl-2-cephem-4-carboxylic acid as a brown froth. The crude acid dissolved in 200 ml. of acetone, was oxidized with 1.15 eq. of chromic acid. The oxidation mixture was allowed to stir at room temperature for five minutes. After five minutes the reaction mixture was evaporated in vacuo to dryness. The residue thereby obtained was dissolved in an ethyl acetate/water slurry. The ethyl acetate layer was separated, washed with brine, dried over anhydrous sodium sulfate, and evaporated in vacuo to dryness to provide 637 mg. of 7-(2-thienylacetamido)-7-methoxy-3-formyl-2-cephem-4-carboxylic acid as a froth. The acid, dissolved in 3 ml. of acetone and 100 ml. of ethyl acetate, was reacted with excess diphenyldiazomethane. The mixture was heated to reflux and then allowed to cool to room temperature. Chromatography on 10.0 g. of silica gel using a toluene-ethyl acetate gradient provided 0.509 g. (33.8 percent) of a white froth, the nmr spectrum of which showed it to be a mixture of the benzhydryl ester of the starting 3-acetoxymethyl-2-cephem and the title product, benzhydryl 7-(2-thienylacetamido)-7-methoxy-3-formyl-2-cephem-4-carboxylate: nmr (CDCl$_3$) 3.40 (s, 3, OCH$_3$), 3.84 (s, 2, side chain CH$_2$), 5.44 (s, 1, C$_6$—H), 5.60 (s, 1, C$_4$—H), 4.88 (C$_2$—H) and 9.20 (s, 1, —CHO).

EXAMPLE 26

Benzhydryl 7-(2-thienylacetamido)-7-methoxy-3-(1-hydroxyethyl)-2-cephem-4-carboxylate.

The crude benzhydryl 7-(2-thienylacetamido)-7-methoxy-3-formyl-2-cephem-4-carboxylate (0.509 g., from previous example) was dissolved in 6 ml. of dry tetrahydrofuran. After degassing the solution with argon/vacuum, and cooling under an argon atmosphere to −74° C., 0.93 ml. of 3.0 M. methylmagnesium bromide in tetrahydrofuran was added. The solution immediately turned brown and thickened. After four minutes, 2 ml. of 1N.HCl was added. The mixture was allowed to warm to 0° C. and was transferred to a separatory funnel with the aid of cold ethyl acetate. The solution was washed successively with cold 1N.HCl (2X), water, and brine, and then dried over anhydrous sodium sulfate. Evaporation in vacuo to dryness provided 0.466 g. of a froth which was chromatographed on 10.0 g. of silica gel using a toluene-ethyl acetate gradient. The following compounds, listed in the order of their elution from the column, were isolated:

benzhydryl 7-(2-thienylacetamido)-7-methoxy-3-acetoxy-2-cephem-4-carboxylate (179 mg.), an unaltered contaminant of the starting material;

benzhydryl 7-(2-thienylacetamido)-7-methoxy-3-(1-hydroxyethyl)-2-cephem-4-carboxylate (154 mg., 45.3 percent);
ir (CHCl$_3$) 1779 cm$^{-1}$ (β-lactam C = O); nmr (CDCl$_3$) δ1.17 (d, 3, J = 6.0 Hz, —CH(OH)C$\underline{H}_3$), 2.9 (broad s, 1, OH), 3.42 (s, 3, OCH$_3$), 3.83 (s, 2, side chain CH$_2$), 4.3 (m, 1, —C$\underline{H}$(OH)CH$_3$), and 5.32 (s, 1, C$_6$—H); and 7-(2-thienylacetamido)-7-methoxy-3-(1-hydroxyethyl)-3-cephem-4-carboxylic acid lactone (36 mg., 15.6 percent); white crystals from methylene chloride-hexane (m.p. 197–198 dec.):
nmr (CDCl$_3$) δ1.50 (d, 3, J = 8.0 Hz), 3.52 (s, 3, OCH$_3$), 3.95 (s, 2, side chain CH$_2$), 5.10 (s, 1, C$_6$—H).

Analysis Calcd. for C$_{16}$H$_{16}$N$_2$O$_5$S$_2$: C, 50.51; H, 4.24; N, 7.36; Found: C, 50.25; H, 4.13; N, 7.25.

EXAMPLE 27

Benzhydryl 7-(2-thienylacetamido)-7-methoxy-3-acetyl-2-cephem-4-carboxylate.

To a solution of 0.154 g. of benzhydryl 7-(2-thienylacetamido)-7-methoxy-3-(1-hydroxyethyl)-2-cephem-4-carboxylate in 40 ml. of acetone was added 1.5 eq. of chromic acid. After stirring the mixture at room temperature for 10 minutes, 2 ml. of isopropanol was added. After stirring for an additional 5 minutes, the reaction mixture was evaporated in vacuo to dryness. The residue was dissolved in an ethyl acetate/water slurry. The organic layer was separated, washed successively with water (2X), aqueous sodium bicarbonate solution, 1N.HCl, and brine and dried over anhydrous sodium sulfate. Evaporation in vacuo to dryness provided product which was chromatographed on 5.0 g. of silica gel using a toluene-ethyl acetate gradient to give 0.073 g. (47.8 percent) of the title product as a white froth:
ir (CHCl$_3$), 1783 cm$^{-1}$ (β-lactam C = O); nmr (CDCl$_3$) δ2.27 (s, 3,

3.43 (s, 3, OCH$_3$), 3.88 (s, 2, side chain CH$_2$), 5.20 (s, 1, C$_6$—H), 5.73 (s, 1, C$_4$—H) and 7.56 (s, 1, C$_2$—H).

EXAMPLE 28

Benzhydryl 7-(2-thienylacetamido)-7-methoxy-3-acetyl-3-cephem-4-carboxylate 1-oxide.

Benzhydryl 7-(2-thienylacetamido)-7-methoxy-3-acetyl-2-cephem-4-carboxylate (Example 27) was oxidized in accordance with the procedure of Example 6 supra. The product sulfoxide crystallized from methylene chloride/hexane as white needles (m.p. 214°–215° dec.).

Analysis Calcd. for $C_{28}H_{24}N_2O_6S_2$: C, 60.19; H, 4.53; N, 4.84; Found: C, 60.44; H, 4.50; N, 5.07.

EXAMPLE 29

Benzhydryl 7-(2-thienylacetamido)-3-acetyl-2-cephem-4-carboxylate.

To a cooled (−73° C.), stirred solution of 0.557 g. of benzhydryl 7-(2-thienylacetamido)-3-ethylcarbonyldioxy-2-cephem-4-carboxylate in 30 ml. of dry tetrahydrofuran under argon was added 0.612 ml. of a 3 molar methylmagnesium bromide solution. After about 3 minutes, 5 ml. of 1N.HCl was added.

The resulting solution was allowed to warm to 0° C. The mixture was then transferred to a separatory funnel with the aid of ethyl acetate and washed with 1N.HCl and brine and dried over anhydrous sodium sulfate. Evaporation in vacuo to dryness provided a product which was chromatographed on a silica gel column using a benzene-ethyl acetate gradient to give 0.193 g. (40 percent) of the title product and 0.230 g. (41 percent) of benzhydryl 7-(2-thienylacetamido)-3-carboxy-2-cephem-4-carboxylate. The nmr spectrum of the product ketone was identical to that of the ketone prepared by the oxidation of the corresponding secondary carbinol.

I claim:
1. The compound of the formula

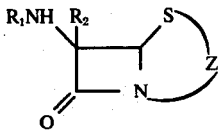

wherein Z is a group of the formula

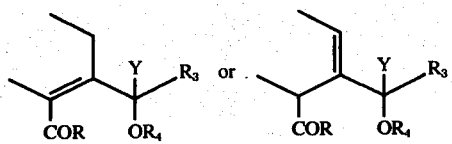

wherein R is a group of the formula $-OR_5$ wherein
$R_5$ is hydrogen or a carboxylic acid protecting ester forming group;
$R_4$ taken together with Y forms a carbon-oxygen double bond; and
$R_3$ is $C_1-C_6$ alkyl, vinyl, allyl, ethynyl, benzyl, or phenyl; and
$R_1$ is an acyl group of the formula

wherein R' is
(a) $C_1-C_6$ alkyl, $C_3-C_7$ alkenyl, cyanomethyl, halomethyl, 4-amino-4-carboxybutyl, 4-protected amino-4-protected carboxybutyl; or
(b) benzyloxy, 4-nitrobenzyloxy or 4-methoxybenzyloxy; or
(c) the group —R'' wherein R'' is 1,4-cyclohexadienyl, phenyl or substituted phenyl wherein the substituents are 1-3 halogens, hydroxy, nitro, cyano, trifluoromethyl, $C_1-C_4$ alkyl, $C_1-C_4$ alkoxy, carboxy, carboxymethyl, hydroxymethyl, aminomethyl or protected aminomethyl; or
(d) an arylalkyl group of the formula

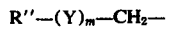

wherein R'' is as defined above,
Y is O or S, and
m is 0 or 1; or
(e) a substituted arylalkyl group of the formula

wherein R''' is R'' as defined above, 2-thienyl or 3-thienyl, W is hydroxy or protected hydroxy, carboxy or protected carboxy, amino or protected amino; or
(f) a heteroarylmethyl group of the formula

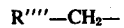

wherein R'''' is 2-thienyl, 3-thienyl, 2-furyl, 3-furyl, 2-thiazolyl, 5-tetrazolyl or 1-tetrazolyl; and
$R_2$ is hydrogen or methoxy; and when $R_5$ is hydrogen, the pharmaceutically acceptable non-toxic salts of the acids represented thereby.
2. The compound of claim 1 wherein $R_5$ is hydrogen, tert-butyl, benzyl, 4-methoxybenzyl, $C_2-C_6$ alkanoyloxymethyl, 2-iodoethyl, 4-nitrobenzyl, diphenylmethyl (benzhydryl), phenacyl, p-halophenacyl, dimethylallyl or 2,2,2-trichloroethyl.
3. The compound of claim 2 wherein $R_5$ is hydrogen.
4. The compound of claim 1 wherein $R_3$ is $C_1-C_3$ alkyl, benzyl or phenyl.
5. The compound of claim 4 wherein $R_5$ is hydrogen.
6. The compound of claim 4 wherein R' is an arylalkyl group of the formula $R''-(Y)_m-CH_2-$.
7. The compound of claim 4 wherein R' is a heteroarylalkyl group of the formula $R''''CH_2-$.
8. The compound of claim 7 wherein R' is 2-thienylmethyl.
9. The compound of claim 8 said compound being 7-(2-thienylacetamido)-3-propionyl-3-cephem-4-carboxylic acid.
10. The compound of claim 8 said compound being 7-(2-thienylacetamido)-3-benzoyl-3-cephem-4-carboxylic acid.
11. The compound of claim 8 said compound being 7-(2-thienylacetamido)-7-methoxy-3-acetyl-3-cephem-4-carboxylic acid.
12. The compound of claim 4 wherein R' is a substituted arylalkyl group of the formula

13. The compound of claim 12 wherein W is hydroxy, or hydroxy derived formyloxy, chloroacetoxy, benzyloxy, benzhydryloxy, trityloxy, 4-nitrobenzyloxy, 4-methoxybenzyloxy, trimethylsilyloxy; carboxy, or carboxy derived tert-butoxycarbonyl, benzyloxycarbonyl, 4-methoxybenzyloxycarbonyl, 2-iodoethoxycarbonyl, 4-nitrobenzyloxycarbonyl, benzhydryloxycarbonyl, phenacyloxycarbonyl, p-halophenacyloxycarbonyl, 2,2,2-trichloroethoxycarbonyl, dimethylallyloxycarbonyl; or amino, or amino derived tert-butoxycarbonylamino, benzyloxycarbonylamino, 4-methoxybenzyloxycarbonylamino, 4-nitrobenzyloxycarbonylamino, 2,2,2-trichloroethoxycarbonylamino, or 1-carbomethoxy-2-propenylamino.

14. The compound of claim 13 said compound being 7-(2-formyloxy-2-phenylacetamido)-3-acetyl-3-cephem-4-carboxylic acid.

15. The compound of claim 13 wherein $R_2$ is methoxy.